United States Patent
Barge et al.

[19]

[11] Patent Number: 5,989,688

[45] Date of Patent: Nov. 23, 1999

[54] COMPOSITE NONWOVENS AND METHODS FOR THE PREPARATION THEREOF

[75] Inventors: Patrick Barge, Réguisheim; Mimoun Saim, Raedersheim; Frédéric Rose, Vogelsheim; Katharine Dyrmose-Jensen, Thann, all of France

[73] Assignee: Jacob Holm Industries (France) SAS, Soultz, France

[21] Appl. No.: 08/730,660

[22] Filed: Oct. 11, 1996

Related U.S. Application Data

[60] Provisional application No. 60/011,385, Feb. 9, 1996.

[30] Foreign Application Priority Data

Oct. 11, 1995 [EP] European Pat. Off. ............. 95402278

[51] Int. Cl.$^6$ ............................ B32B 27/14; A61F 13/15; B60B 33/08

[52] U.S. Cl. ......................... 428/198; 442/381; 442/382; 442/389; 428/219; 604/370; 16/26; 156/285; 156/286; 156/308.2; 156/73.1

[58] Field of Search ................................... 428/219, 198; 604/370; 442/381, 382, 389; 16/26; 156/285, 286, 308.2, 73.1

[56] References Cited

U.S. PATENT DOCUMENTS

| | | | |
|---|---|---|---|
| 4,355,066 | 10/1982 | Newman | 428/198 |
| 4,883,707 | 11/1989 | Newkirk | 428/219 |
| 4,892,534 | 1/1990 | Datta et al. | 604/370 |
| 5,300,054 | 4/1994 | Feist et al. | 604/378 |
| 5,427,845 | 6/1995 | Sawyer et al. | 428/288 |
| 5,584,101 | 12/1996 | Brabant et al. | 19/304 |
| 5,752,945 | 5/1998 | Mosley et al. | 604/370 |

FOREIGN PATENT DOCUMENTS

| | | | |
|---|---|---|---|
| 0359501 | 3/1990 | European Pat. Off. | |
| 0359501A2 | 3/1990 | European Pat. Off. | |
| 0480724A1 | 4/1992 | European Pat. Off. | D21H 27/42 |
| 0532005 | 3/1993 | European Pat. Off. | |
| 0539703 | 5/1993 | European Pat. Off. | |
| 0596191 | 5/1994 | European Pat. Off. | |
| 2690843 | 11/1993 | France | |
| 2272859 | 6/1994 | United Kingdom | |
| 2278371 | 11/1994 | United Kingdom | |
| WO94/12713 | 6/1994 | WIPO | |
| WO94/14397 | 7/1994 | WIPO | |
| WO94/19179 | 9/1994 | WIPO | B32B 5/26 |
| WO94/22393 | 10/1994 | WIPO | |
| WO94/28222 | 12/1994 | WIPO | |
| WO95/13776 | 5/1995 | WIPO | |

Primary Examiner—Jeffrey Stucker
Assistant Examiner—Hankyel T. Park
Attorney, Agent, or Firm—Birch, Stewart, Kolasch & Birch, LLP

[57] ABSTRACT

A composite nonwoven for controlled acquisition and distribution of liquid, comprising at least a first support layer and a first bulky layer, the bulky layer functioning to acquire and distribute liquid and the support layer being suitable for use either as a coverstock or as a transfer layer between the bulky layer and a liquid retention layer, the support layer and the bulky layer being bonded together, by non-chemical bonding, by a network of individual bonding points to form a liquid control system that facilitates liquid distribution within the individual layers and liquid transfer between the layers, the composite nonwoven showing a combination of a low strike-through time and a low rewet; and a high-speed in-line process for producing the composite nonwoven, the process comprising forming a first support layer, e.g. by carding or spunbonding, consolidating the first support layer, forming at least a first bulky layer containing carded fibers on top of the first support layer, and bonding the combination of the support layer and the bulky layer by non-chemical bonding means, e.g. thermobonding, during which process draft is reduced at least during formation of the first bulky layer by means of at least one laydown suction box providing suction at least at the point at which the bulky layer is formed and by means of at least one holddown suction box providing suction after formation of the bulky layer and until the point at which bonding between the layers takes place, said laydown and holddown suction boxes being located beneath an air-permeable conveyor belt.

30 Claims, 8 Drawing Sheets

3 * Strike Through

COMPOSITE NONWOVENS AND METHODS FOR THE PREPARATION THEREOF

This application claims priority on provisional application Ser. No. 60/011,385 filed on Feb. 9, 1996, the entire contents of which are hereby incorporated by reference.

FIELD OF THE INVENTION

The present invention relates to multilayer composite nonwovens designed to acquire, distribute and transfer liquids in hygienic absorbent articles, and to methods for the preparation of such composite nonwovens.

BACKGROUND OF THE INVENTION

Hygienic absorbent products such as disposable diapers, feminine hygiene products and adult incontinence pads consist of a number of different layers, including a liquid permeable "topsheet" or "coverstock" layer which in use is located against the skin of the wearer, an absorbent core for retaining liquid and a liquid impermeable "backsheet" away from the skin of the wearer to maintain the absorbed liquid inside of the absorbent product. Additional layers are commonly provided with the aim of obtaining the desired characteristics in terms of acquisition and distribution of liquid, and the construction and function of such hygienic absorbent products is the subject of numerous patents and patent applications.

Although the characteristics of hygienic absorbent articles can vary depending upon the intended use, a few basic characteristics are generally sought, in particular the ability to absorb liquid at a sufficient rate and the ability to hold the absorbed liquid within the absorbent article, in addition to features such as comfort for the wearer and ease of production. Although such absorbent articles have undergone many advances in recent years, significant efforts continue to be made to improve their characteristics and to develop absorbent articles that are specially designed for specific uses. This has led to the development of a number of different composite nonwovens for the acquisition, distribution and/or storage of liquid in hygienic absorbent articles, some examples of which are the following:

EP 0 359 501-B1 discloses an absorbent structure containing cover, transfer and reservoir layers, each of which has preselected fluid retention and transfer capacity, in which the cover layer has a lower density than the transfer layer and tends to promote transfer of liquid to the transfer layer, and the transfer layer has a lower density than the reservoir layer and tends to promote transfer to the reservoir layer.

EP 0 532 005-A1 describes absorbent articles containing a backsheet layer, an absorbent body, an intermediate transfer layer and a bodyside liner layer, the bodyside liner layer being a bonded carded web composed of bicomponent fibres and having a basis weight of 15–40 g/m$^2$.

EP 0 539 703-A1 discloses an absorbent article that includes, between a topsheet and a backsheet, an absorbent body containing a retention portion and, adjacent the topsheet, a surge management layer comprising bicomponent fibres and optionally also non-bicomponent fibres.

EP 0 596 191-A1 discloses a fibrous laminated material in which the two fibrous layers are bonded together in a bonding pattern with discrete bonding areas containing apertures, the first fibrous layer comprising fibres of one or more thermoplastic polymeric materials and the second fibrous layer comprising fibres of two or more thermoplastic polymeric materials.

FR 2 690 843-A1 discloses a process for manufacturing multilayer nonwovens in which a nonwoven web is formed on each of two different shaping cylinders, the webs then being joined together on a suction cylinder.

U.S. Pat. No. 4,892,534 discloses a nonwoven web for use as a bodyside liner, in particular for feminine pads, and containing at least 3 layers of thermoplastic filaments bonded together, the web being formed by spunbonding.

U.S. Pat. No. 5,300,054 discloses absorbent articles in which the absorbent core comprises pairs of layers, where each pair of layers comprises an acquisition/distribution layer and a storage layer, the storage layer of each pair of layers being located subjacent the acquisition/distribution layer.

WO 94/12713 discloses a multilayer nonwoven material comprising at least two layers of natural or synthetic textile fibres with progressively decreasing fibre denier from one layer to the next.

WO 94/14397 discloses an absorbent structure containing a first surge management layer of polymeric fibres and a second surge management layer of hydrophilic fibres, e.g. cellulosic fibres, with an absorbent layer including a high-absorbency material between the first and second surge management layers.

WO 94/22393 describes a topsheet having three separate layers, namely a first and second polymeric layer with an intermediate fibrous layer between the two polymeric layers, in which the fibrous material of the intermediate layer extends below the inner surface of the second polymeric layer, containing capillaries, e.g. in the form of apertures, that extend from a first surface of the topsheet to a second surface of the topsheet.

WO 94/28222 discloses a composite nonwoven containing at least two layers of carded fibres with progressively decreasing fibre denier from one layer to the next, the layers been joined together by needling.

WO 95/13776 describes absorbent articles containing, in addition to a topsheet, a backsheet and an absorbent core, an acquisition layer between the topsheet and the core, and optionally also an intermediate "liquid stable layer" with a structural support function between the acquisition layer and the core.

Despite the fact that many different composite nonwoven products are known and that many advances have been made in this field in recent years, prior art composite nonwovens for use in hygiene absorbent products suffer from certain disadvantages. One of these is the manner in which liquid is distributed in those nonwoven products having or functioning as an acquisition/distribution layer. Thus, although many nonwovens are designed to provide a certain distribution of absorbed liquid within the acquisition/distribution layer before the liquid is transferred to the absorbent core, this distribution is in general one which could be termed "passive distribution", meaning that liquid is absorbed and in most cases initially flows essentially directly to the absorbent core without any substantial distribution before being transferred to the core layer where liquid is stored. Such absorbent cores normally store liquid with the aid of a super absorbent polymer. These super absorbent polymers are extremely effective, since they are able to absorb many times their own weight of urine or other liquids, but upon wetting they form a gel which, while being effective to hold onto absorbed liquid, has the disadvantage that liquid is not easily transferred through such a gel agglomeration.

This results in a phenomenon known as "gel blocking", in which the first portion of liquid is readily absorbed, while subsequent portions must migrate around the gel area before they can be taken up by other parts of the absorbent core, with the possibility for leakage and retained liquid on the surface of the diaper. It is in this case that the prior art nonwovens distribute and transfer liquid by means of passive distribution, so that subsequent portions of liquid bypass the already wetted and gelled area of the core. With passive distribution, the first portion of liquid thus flows more or less directly to the absorbent core, and it is only subsequent portions that are directed—in a "passive manner" (because of the lack of access there where the core is already wetted)—to other portions of the core. It would thus be desirable to be have an acquisition/distribution layer with a more active distribution function, so that the liquid holding capacity of the absorbent core could be more effectively utilized.

A further problem in the prior art composite nonwovens and absorbent products is that the liquid absorbency rate is often limited by the topsheet. Thus, the "strike-through time" for known topsheets is at the best about 2.5 sec, and it would therefore be desirable to be able to improve the absorbency characteristics of absorbent articles by improving the strike-through time of the topsheet.

Another problem encountered is that of "rewet", i.e. leakage of absorbed liquid from the absorbent core. Prior art composite nonwovens typically have a rewet of not less than about 0.2 g (as determined by EDANA standard No. ERT 151.0-93) and it would be desirable to reduce the rewet value to below 0.2, and preferably as low as possible, thereby ensuring that absorbed liquid is maintained in the absorbent core.

With regard to the methods used for the production of nonwovens, including composite nonwovens, it is a general aim to be able to increase the production speed while at the same time maintaining sufficient strength and uniformity of the nonwovens. The problem arises, however, that an increase in production speed tends to lead to a decrease in strength and uniformity of the resulting nonwoven. In the case of composite nonwovens, it is important to be able to both produce individual layers having sufficient quality at a sufficient speed and to be able to assemble the composite nonwoven in an advantageous manner. A high-speed, in-line process resulting in composite nonwovens with the desired properties in terms of strength, uniformity and absorption characteristics would be particularly desirable. Related to this is the aim of providing a basic production process that is flexible enough to be suitable for producing a variety of different composite nonwovens in terms of varying acquisition and distribution patterns and in which the order of the layers can be adjusted as required.

The above problems associated with prior art composite nonwovens and methods for their production are addressed by the present invention.

BRIEF DISCLOSURE OF THE INVENTION

In one aspect, the present invention relates to a composite nonwoven for controlled acquisition and distribution of liquid, comprising at least a first support layer and a first bulky layer, the bulky layer functioning to acquire and distribute liquid and the support layer being suitable for use either as a coverstock or as a transfer layer between the bulky layer and a liquid retention layer, the support layer and the bulky layer being bonded together, preferably by non-chemical bonding, by a network of individual bonding points to form a liquid control system that facilitates liquid distribution within the individual layers and liquid transfer between the layers, the composite nonwoven showing a combination of a low acquisition time, a low strike-through time after repeated wettings and a low rewet.

In another aspect the invention relates to a high-speed in-line process for producing a composite nonwoven for controlled acquisition and distribution of liquid comprising at least a first support layer and a first bulky layer, the bulky layer functioning to acquire and distribute liquid and the support layer being suitable for use either as a coverstock or as a transfer layer between the bulky layers and a liquid retention layer, the process comprising forming a first support layer, consolidating the first support layer, forming a first bulky layer containing carded fibres on top of the first support layer, and bonding the combination of the support layer and the bulky layer, preferably by non-chemical bonding, to form bonds within the bulky layer and a network of individual bonding points between the first bulky layer and the first support layer that facilitate liquid distribution within the individual layers and liquid transfer between the layers, during which process draft is reduced at least during formation of the first bulky layer by means of at least one laydown suction box providing suction at least at the point at which the bulky layer is formed and by means of at least one holddown suction box providing suction after formation of the bulky layer and until the point at which bonding between the layers takes place, said laydown and holddown suction boxes being located beneath an air-permeable conveyor belt.

DETAILED DESCRIPTION OF THE INVENTION

The term "support layer" as used herein refers to a substantially flat nonwoven layer having a support function with respect to the bulky layer(s) of the composite nonwoven. As will be explained below, the support layer can also have other functions than a support function, e.g. in cases where the support layer also functions as a coverstock in an absorbent article.

The term "bulky layer" refers to a lightweight, low density nonwoven layer, i.e. a layer having a certain bulk or airiness as opposed to the rather flat, dense support layer. Void space in the bulky layer(s) is necessary for fast acquisition of liquid.

The term "network of individual bonding points" refers to the fact that the layers of the composite nonwovens of the invention are bonded together so as to obtain a network of bonding points between the layers, each bonding point between the fibres of a given layer and the fibres of an adjacent layer providing a contact point that facilitates liquid transfer between the layers in question and that provides fabric integrity (holds the fabric together). Similarly, the bonding of fibres within a layer provides contact points that facilitate liquid distribution within the layer in question.

The term "liquid retention layer" refers to a layer or portion of an absorbent article designed to store absorbed liquid, for example an absorbent core of a diaper containing synthetic and/or natural fibres and a superabsorbent polymer.

An advantageous and surprising feature of the composite nonwovens prepared according to the present invention is the fact that they have been found to exhibit both an unusually low strike-through time and low acquisition time (ADD measurement method) and an unusually low rewet even when using a high pressure (ADD wetback method) to provoke "wetback". Thus, the composite nonwovens of the invention may be characterized by a low strike-through time (3rd insult) of at the most about 2.5 sec, typically at the most about 2.0 sec, preferably at the most about 1.5 sec, more preferably at the most about 1.0 sec, as determined by the modified EDANA test method described herein based on EDANA standard No. ERT 150.2-93. The acquisition time measured by the ADD method described below is should for the third insult be no more than about 60 sec, preferably no more than about 40 sec, more preferably no more than about 30 sec, most preferably no more than about 27 sec. The composite nonwovens may also be characterized by a rewet, determined in accordance with EDANA standard No. ERT 151.0-93, of at the most about 0.20 g, preferably at the most about 0.15 g, more preferably at the most about 0.10 g, e.g. no more than about 0.08 g. The advantageous properties in terms of e.g. strike-through time are exhibited regardless of the orientation of the layers, i.e. regardless of whether the support layer is below the bulky layer(s) or is used as a coverstock on top of the bulky layer(s).

The fact that the composite nonwovens of the invention have a combination of low acquisition time (measured by strike-through time or by acquisition time) and low rewet is quite surprising, since a relatively low strike-through in the prior art nonwovens tends to be associated with a relatively high rewet. The reason why this is not the case in the composite nonwovens of the invention is believed to be related to the fact that these composite nonwovens ensure that liquid is actively distributed through the absorbent core, so that the core is more effectively utilized and better able to hold onto absorbed liquid, thereby resulting in a low rewet.

Although a single bulky layer may be suitable in certain cases, it will in most cases be preferred to have an additional bulky layer in order to have a bulky layer portion of the composite nonwoven with greater bulk (more void space), and thus greater capacity to both acquire and distribute liquid. Also, the use of two bulky layers allows the individual layers, and thus the composite nonwoven as a whole, to be adapted to the desired liquid control properties, as will be explained in more detail below. A further advantage of having two bulky layers is that a bulky layer portion formed from two bulky layers will tend to be somewhat more uniform than a single thick bulky layer, since a non-uniformity in a given area of one of the layers will in all probability lie adjacent to a more uniform area of the other bulky layer. The composite nonwovens thus preferably comprise a second bulky layer, where the second bulky layer is bonded by non-chemical means to the first bulky layer by a network of individual bonding points that facilitate liquid distribution and liquid transfer between the bulky layers. For purposes of the present specification, it is to be understood that each and any bulky layer is uniquely and individually designed for specific liquid control behavior, regardless of whether the composite nonwoven contains a single bulky layer or more than one bulky layer.

As will be explained below in connection with the process for producing the composite nonwovens, while it is contemplated that the bulky layers will be produced by carding, the support layer may be produced by a variety of different methods, e.g. it may be spunlaid, wetlaid, drylaid or airlaid, with carding and spunbonding being two preferred methods for producing the support layer. Thus, in the composite nonwovens of the invention, all of the layers may be carded webs, or they may consist of e.g. one or two carded webs together with e.g. a spunbonded web.

The bulky layer(s) will typically comprise a mix of synthetic binder fibres and other (matrix) fibres, but it is also possible to have a bulky layer that consists of only a single type of fibre, typically a bicomponent fibre, but possibly also a monocomponent fibre. In those cases in which the bulky layer contains a mixture of binder fibres and other (matrix) fibres, the binder fibres will typically include bicomponent fibres or monocomponent fibres containing polyethylene, polypropylene, polyester or a copolymer, in which the copolymer is typically a copolymer of polypropylene or polyester. Suitable examples of bicomponent fibres are polypropylene/polyethylene (available from e.g. Danaklon a/s, Denmark), polyester/polyethylene (available from e.g. Dupont or Wellman) and polyester/copolyester bicomponent fibres. A binder fiber can also be a monocomponent fiber with a melting point less than that of the matrix fibre (e.g. polypropylene when the matrix fibre is polyester). The matrix fibres may be selected from synthetic fibres, e.g. polypropylene or polyester, and cellulosic fibres, including viscose/Lyocell fibres. A presently preferred fibre for use together with binder fibres is one of polyester.

The support layer will typically comprise synthetic fibres or filaments, e.g. polypropylene or polyester fibres or filaments, or bicomponent fibres of the type mentioned above, or a mix of synthetic fibres or filaments and cellulosic fibres, e.g. a mix of bicomponent or polypropylene fibres and viscose fibres. Another possibility is a mix of two synthetic fibres, e.g. polypropylene and a polyolefin-based bicomponent fibre. Presently preferred materials for the support layer are polypropylene or bicomponent fibres or filaments, or a blend of polypropylene and polyolefin-based bicomponent fibres.

The fineness of the fibres of the various layers may be varied as required, so as to result in a composite nonwoven with the desired characteristics in terms of liquid control as well as strength, softness, etc. For the support layer, the fibres or filaments will typically have a fineness in the range of 1–7 dtex, preferably 1.5–5 dtex, more preferably 1.7–4.0 dtex, e.g. 1.7–3.3 dtex. When a bulky layer includes bicomponent fibres, these will typically have a similar fineness, i.e. in the range of 1–7 dtex, preferably 1.5–5 dtex, more preferably 1.7–3.3 dtex.

In bulky layers containing both binder fibres and matrix fibres, the majority of the fibres will often be matrix fibres. The percentage of binder fibres in the bulky layer(s) will thus typically be in the range of 10–65% by weight, e.g. 15–50% by weight, more typically 20–40% by weight, such as about 25–35% by weight, based on the total weight of the bulky layer(s). In certain cases, however, one or more bulky layer may consist essentially of bicomponent fibres. The matrix fibres in the bulky layers will typically have a fineness in the range of 1–12 dtex, the fineness of the matrix fibres in any given bulky layer being adapted to the desired liquid control characteristics, i.e. according to whether the layer in question is to have primarily an acquisition, distribution or transfer function. Similarly, when the composite nonwoven comprises two bulky layers, the relationship of the fineness of the fibres in the first bulky layer to the fineness of the fibres in the second bulky layer will in part be determined by the manner in which the two layers are intended to function relative to each other and to the coverstock and absorbent core, so that the result is a liquid control system with the desired features.

For example, for a composite nonwoven containing a first bulky layer designed primarily for acquisition of liquid and a second bulky layer designed primarily for distribution of liquid within the layer, the first bulky layer will typically comprise fibres in the range of about 5–12 dtex, which facilitates low retention and high liquid transfer through this layer, thereby allowing the surface of the absorbent article to remain dry, while the second bulky layer will typically comprise somewhat finer fibres, e.g. having a fineness in the range of from 1 to less than 5, which allows for good distribution and ultimately a high utilization of the core. When considering the fineness of the fibres in a layer, it will be understood to persons skilled in the art, however, that fibre fineness is only one parameter influencing the liquid control characteristics, and that other parameters such as fibre treatment/surface tension (hydrophilic/hydrophobic), pore volume and the fineness of the fibres in a given layer compared to that of fibres of adjacent layers are also of importance.

With regard to functional characteristics, the composite nonwovens of the present invention (or individual layers thereof) may be divided into a number of different categories based on their relative functions in terms of liquid acquisition, distribution and transfer. The basic groupings and their important properties are shown below, and the different types are further illustrated in the examples, which also describe the test methods used and the results of these tests.

| Type | Properties |
|---|---|
| Acquisition (A) | low strike-through |
| | low retention |
| | high absorbency 180 sec |
| | low acquisition time (ADD method) |
| Distribution (D) | high absorbency 5 sec |
| Transfer (T) | low retention |
| | low strike-through |
| | low acquisition time (ADD method) |

Since the composite nonwovens of the present invention are designed for acquisition and distribution of aqueous liquids such as urine, any polyolefin or polyester fibres or filaments used (e.g. polypropylene fibres or bicomponent fibres containing a polyolefin component) will in most cases preferably have been treated so as to provide them with sufficient hydrophilic properties. The treatment of such fibres to render them hydrophilic may be performed in a manner known in the art, e.g. by application of a hydrophilic spin finish to the surface of the fibres or by incorporating a surface active agent into the sheath component of a sheath-core type bicomponent fibre, the latter method being described in WO 89/10989. A preferred method of rendering such fibres hydrophilic is by treating them with a permanent hydrophilic spin finish to obtain good liquid control properties at repeated mictions, e.g. a spin finish of the type described in international patent application No. PCT/DK96/00178.

The bulky layer(s) may comprise fibres with a bi- or tri-dimensional crimp, and may also comprise hollow fibres. In addition to added bulk for the same dtex obtained by using 3-dimensional or hollow fibres, the use of hollow fibres allows the pore volume and capillary effects to be controlled, as is illustrated in the examples below. The hollow fibres and fibres with tri-dimensional crimp also allow for a better bulk recovery, which is very important as the composite nonwoven material when incorporated in an absorbent product will during transportation and storage be submitted to high pressure. It is therefore important that the material is able to quickly regain its original bulky state in order to provide the desired acquisition and distribution properties when in use.

The support layer in the composite nonwovens of the present invention will typically have a basis weight of at the most 20 $g/m^2$, preferably at the most 16 $g/m^2$, e.g. 10–15 $g/m^2$, the support layer ideally being as lightweight as possible while still having the necessary strength to be able to fulfill a support function for the bulky layers. A support layer with a basis weight of less than 10 $g/m^2$ is therefore also of interest, e.g. a basis weight of 8 or 9 $g/m^2$ or even lower, such as 6 or 7 $g/m^2$, as long as the support layer has the necessary strength. The total basis weight of the bulky layer(s) may suitably be in the range of 8–60 $g/m^2$, e.g. 12–40 $g/m^2$, such as 16–40 $g/m^2$. Lower basis weights may, however, also be of interest for the bulky layer(s). When the composite nonwoven contains two bulky layers, their total basis weight may suitably be less than 25 $g/m^2$, e.g. at the most about 24 $g/m^2$, such as at the most about 20 $g/m^2$. Also interesting are lightweight products in which the total weight of the two bulky layers is e.g. in the range of 12–19 $g/m^2$, e.g. 14–18 $g/m^2$, such as about 15–16 $g/m^2$. For products containing only a single bulky layer, this may suitably be a lightweight layer of e.g. at the most about 20 $g/m^2$, e.g. in the range of 6–18 $g/m^2$, such as 8–14 $g/m^2$.

The total weight of the composite nonwoven of the invention may, for lightweight products, thus suitably be at the most about 25 $g/m^2$, e.g. at the most about 24 or 22 $g/m^2$ or even less, such as at the most about 20 or 18 $g/m^2$ for particularly lightweight products.

One of the advantages of the composite nonwovens of the present invention and, as will be further explained below, the process for producing them, is the fact that they provide a very large degree of flexibility in that the characteristics of the individual layers as well as the arrangement of the layers relative to one another can be varied to provide the desired product features. The present invention thus provides a "liquid control system" that allows for a desired pattern of acquisition and distribution of liquid within the composite nonwoven of the invention, which in turn makes it possible to more efficiently utilize the absorption capacity of the absorbent core in hygiene absorbent products. A particular advantage of the present invention is that the arrangement of the layers in the liquid control system can be altered so that the support layer can function not only as a support layer located below the bulky layers, but also as a coverstock in an absorbent product such as a baby diaper, sanitary napkin or incontinence product. As mentioned above, the composite nonwovens of the invention have been found to have very low strike-through times, thereby allowing optimization of the strike-through time (acquisition time) when the support layer is used as a coverstock or improvement of the liquid transfer to the absorbent core when the support layer is used as a transfer layer between the bulky layers and the core, in both cases allowing the top layer of a diaper to remain dry.

As mentioned above, the composite nonwovens of the present invention may be produced by means of a high-speed in-line process comprising forming a first support layer, consolidating the first support layer, forming a first bulky layer containing carded fibres on top of the first support layer, and bonding the combination of the support layer and the bulky layer by non-chemical bonding, during which process draft is reduced during formation of at least the first bulky layer by means of at least one laydown suction box providing suction at the point at which the bulky layer is formed and by means of at least one holddown suction box providing suction after formation of the bulky layer and until the point at which bonding between the layers takes place, said laydown and holddown suction boxes being located beneath an air-permeable conveyor belt, so as to maintain the structure of the individual layers on the conveyor belt.

The term "high-speed in-line process" refers to the fact that the process of the invention is designed to be operated at high speeds, e.g. at least 150–200 m/min, and preferably e.g. at least 300 m/min, and that the individual layers of the composite nonwoven are produced successively in a single process using a single production line.

Although it is possible may means of the process according to the invention to produce a composite nonwoven with more than one support layer, e.g. containing in sequence a first support layer, a first bulky layer, a second bulky layer and second support layer (e.g. in which one of the support layers functions as a topsheet and the other support layer facilitates transfer of liquid from the bulky layers to the absorbent core), it is contemplated that composite nonwovens prepared according to the invention will in most cases contain a single support layer. The support layer may be produced by a variety of different methods and may thus e.g. be a carded, spunlaid, wetlaid, drylaid or airlaid web. Two presently preferred methods of producing the support layer are by carding or spunbonding. Consolidation of the support layer may be performed by any suitable means, e.g. thermobonding using calender bonding or a hot-air oven, or infrared or ultrasonic bonding. A preferred method for consolidating the support layer is calender bonding.

In the case of a carded support layer, draft is preferably reduced from the card exit point and until the point at which consolidation of the support layer takes place by means of an air-permeable conveyor belt and at least one suction box, and preferably a series of suction boxes, i.e. a laydown suction box providing suction at the point at which the support layer is formed and at least one holddown suction box providing suction after formation of the support layer and until the point at which consolidation of the support layer takes place. This ensures that the support layer maintains a uniform structure, which in turn is important for obtaining high nonwoven strength, in particular at high carding speeds.

When consolidation is performed by means of calender bonding, this preferably includes an arrangement between the conveyor belt and the calender rolls that allows one of the calender rolls (the "upper" calender roll) to function as a rotating support for the unbonded first support layer, and in which the conveyor belt has a reduced diameter conveyor head roll that allows a reduced distance between the conveyor head roll and the upper and lower calender rolls (the terms "upper" and "lower" referring to the normal arrangement of the two calender rolls in a calender bonding means, even though the "upper" calender roll need not necessarily be placed directly above the "lower" calender roll), e.g. as explained below in connection with the drawings.

As mentioned above, the composite nonwovens of the present invention preferably include two bulky layers, and the process for producing the nonwovens therefore preferably further includes the step of forming a second bulky layer on top of the first bulky layer before bonding of the first support layer and the first bulky layer, the second bulky layer being subsequently bonded to the first bulky layer by a network of individual bonding points that facilitate liquid distribution within the second bulky layer and liquid transfer between the bulky layers. Of course, it is also possible to provide further bulky layers, although two bulky layers will generally be sufficient to obtain the desired bulk and uniformity as well as the desired liquid control properties.

When a second bulky layer is provided, this may advantageously be formed using a second card in opposite orientation to the card forming the first bulky layer, and using a perforated suction roll at the point at which the second bulky layer is laid onto the first bulky layer. As is the case with the production of the first support layer and the first bulky layer, it has been found that draft can be reduced during formation of the second bulky layer by means of at least one suction box providing suction between the card exit for the second bulky layer and the perforated suction roll. Such an arrangement of the second card is of great advantage in terms of maintaining a uniform structure of the second bulky layer and of improving cohesion and bonding between the first bulky layer and the second bulky layer. This is explained in further detail below in connection with the accompanying drawings.

Regardless of the number of bulky layers present in the composite nonwoven, it is preferred that substantially the entire length of the production line until the point at which bonding of the composite nonwoven takes place is provided with suction boxes under the conveyor belts in order to reduce draft and maintain a uniform structure of the nonwoven prior to bonding. An example of such a production line provided with a series of suction boxes is given below with reference to the drawings. The use of suction boxes of this type in connection with a high-speed carding line is further described in international patent application No. PCT/EP96/01077, to which reference is made.

When the individual layers that form the composite nonwoven, i.e. the first support layer, the first bulky layer and, typically, the second bulky layer, have been formed, it is then necessary to subject the layers to a bonding process in order to bond the individual layers to one another and to form bonds between the fibres within each of the bulky layers. As mentioned above, this preferably takes place using a non-chemical bonding means, i.e. without "gluing" of the layers to each other. Examples of non-chemical bonding means are thermobonding, hydroentanglement and needle punching. It is preferred, however, that bonding at this stage is performed by thermobonding, in particular using a hot-air oven, or by infrared or ultrasonic bonding.

In a preferred embodiment, bonding of the first bulky layer to the first support layer and, when present, to the second bulky layer, is performed using a through-air oven, in particular one with a drum which can be adjusted to allow either the support layer or the first bulky layer or, when present, the second bulky layer to be in contact with the drum. This provides an advantage in terms of flexibility of the final product, since the surface of the layer which is in contact with the drum of the oven will, as a result of the heating provided by the smooth surface of the drum, correspondingly have a more smooth surface than the opposite surface of the composite nonwoven that is not in contact with the drum. This in turn allows the characteristics of the final product to be altered according to the orientation of the nonwoven in the oven, i.e. depending on whether the support layer side or the bulky layer side is in contact with the drum. Such adjustable through-air ovens are known, but provide a particular advantage in connection with the present invention by augmenting the flexibility which is otherwise provided by the process as a whole.

Due to the extensive use of suction boxes in the process of the invention to maintain the uniform structure of the fibrous webs prior to consolidation thereof, a large amount of air must be circulated. In order to conserve energy and reduce costs, it is therefore preferred that the air sucked from each suction box is recycled, filtered and adjusted to a desired temperature and relative humidity by an air conditioning system. In addition to cost and energy savings, a further advantage of such an air recycling system is that it facilitates the maintenance of a uniform temperature and relative humidity in the process air, thereby helping to obtain more uniform composite nonwovens independent of the temperature and humidity of the outside air. With regard to relative humidity, it is particularly preferred that air whose relative humidity has been adjusted to about 45–65% is sucked through the fibrous webs and the underlying conveyor belts, since this has been found to reduce static electricity repellency between the conveyor belts, which typically are made of synthetic materials, and the synthetic fibres or filaments.

DESCRIPTION OF THE DRAWINGS

In FIG. 1, the prior art card outlet comprises a fibrous web 1 falling by means of gravity from the take off roller 2 (which is part of the card; not shown) onto a conveyor belt 3. In the prior art arrangement the conveyor belt 3 is normally not air-permeable. In order to remove the fibres of the fibrous web 1 away from the take off roller 2, the speed of the conveyor belt 3 is higher than the speed at the surface of the take off roller 2, this speed difference being known as "draft". Due to the draft, the structure of the fibrous web 1 on the take off roller 2 is not the same as on the conveyor belt 3. The draft percentage is given by the following formula:

Draft [%]=100×[(conveyor belt speed/card takeoff speed)−1]

Figure 2:
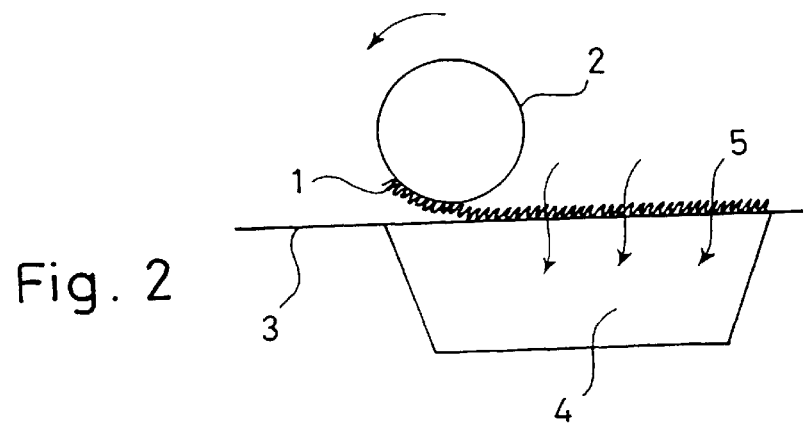
FIG. 2 shows a cross-sectional view of a preferred card outlet used according to the present invention.

In FIG. 2, the card outlet of the invention comprises a fibrous web 1 being taken off the take off roller 2 (which is part of the card; not shown) and being sucked against an air-permeable conveyor belt 3, e.g. a wire mesh belt, by the action of a suction box 4 located under the conveyor belt 3. Air 5 which is sucked through the fibrous web 1 and the conveyor belt 3 actively removes the fibrous web 1 from the take off roller 2, so that the speed of the conveyor belt 3 can be adjusted to the speed of the take off roller 2. This results in a very low draft, so that the structure of the fibrous web 1 is not destroyed during the process.

Figure 1:
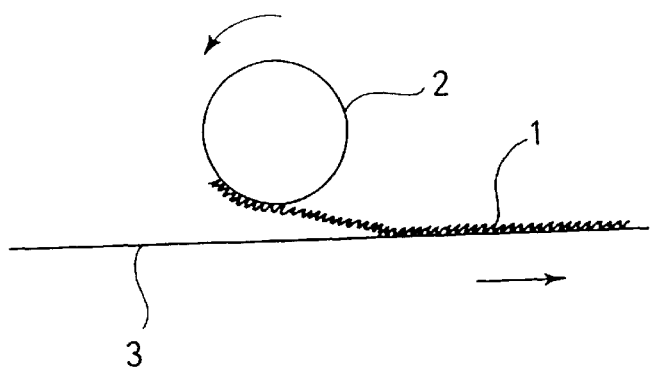
FIG. 1 shows a cross-sectional view of a prior art card outlet.

The following table shows typical values for the draft at different speeds using the conventional card outlet shown in FIG. 1 and using the card outlet of the invention with a suction box as shown in FIG. 2.

| Line speed [m/min] | DRAFT using a conventional card outlet [%] | DRAFT using the card outlet of the invention [%] |
|---|---|---|
| 100 | 12 | 5 |
| 200 | 35 | 13 |
| 300 | impossible | 27 |

Figure 3:
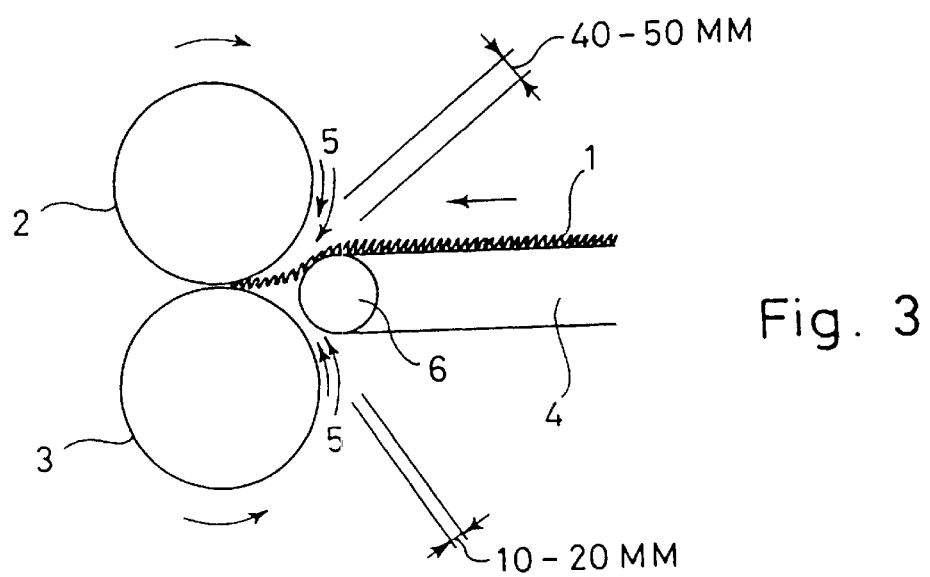
FIG. 3 shows a cross-sectional view of a prior art calender bonding arrangement.
Figure 4:
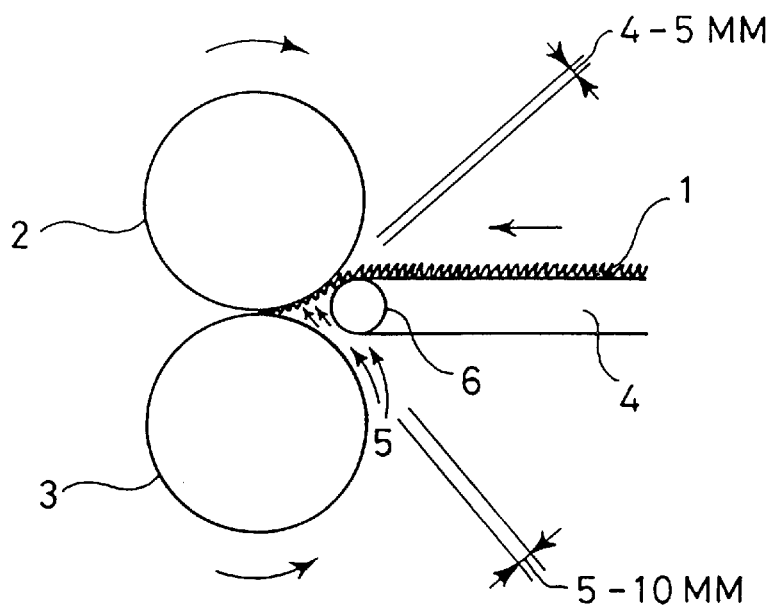
FIG. 4 shows a cross-sectional view of a preferred calender bonding arrangement according to the present invention.

FIGS. 3 and 4 show a comparison between draft exerted on a carded nonwoven web during calender bonding in a conventional arrangement compared to a preferred arrangement according to the present invention.

In FIG. 3, a fibrous web 1 is calender bonded between calender rolls 2 and 3. The fibrous web 1 is transported on a conveyor belt 4 but is not supported once having left the conveyor belt 4 and before reaching the nip between the calender rolls 2 and 3. To avoid the formation of bubbles and folds in the unbonded fibrous web 1 induced by air streams 5 created by the rotation of the hot, large diameter calender rolls 2 and 3, it is necessary for the calender rolls 2 and 3 to pull the nonwoven, thus resulting in "draft" between the calender rolls 2 and 3 and the conveyor belt 4. In this arrangement, the diameter of the conveyor head roll 6 is normally about 200–250 mm, and the distance between the conveyor head roll 6 and calender roll 3 is typically 10–20 mm, while the distance between the conveyor head roll 6 and calender roll 2 is typically 40–50 mm.

In FIG. 4, a calender arrangement according to the invention uses new and advantageous settings between the conveyor belt 4 and the calender rolls 2 and 3. In this case, an air stream 5 coming up with calender roll 3 is used to push the unbonded fibrous web 1 against the top calender roll 2, so that this calender roll 2 acts as a rotating support for the fibrous web 1. In order to reduce the distance between the conveyor belt 4 and the nip between the calender rolls 2 and 3 as much as possible, the conveyor head roll 6 has a special construction with a diameter of approximately 100 mm, and the distance between the conveyor head roll 6 and calender roll 3 is reduced to about 5–10 mm, while the distance between the conveyor head roll 6 and the top calender roll 2 is only 4–5 mm, i.e. essentially the same as or at least not significantly greater than the thickness of the fibrous web 1.

The following table shows typical values for the draft at different speeds between the conveyor belt 4 and the calender rolls 2 and 3 using the conventional arrangement shown in FIG. 3 and using the arrangement of the invention shown in FIG. 4. A suction box (not shown) may optionally be located beneath the conveyor belt 4.

| Line speed [m/min] | DRAFT with conventional arrangement [%] | DRAFT with arrangement of the invention [%] |
|---|---|---|
| 100 | 12 | 3 |
| 200 | 24 | 9 |
| 300 | 36 | 19 |

Figure 5:
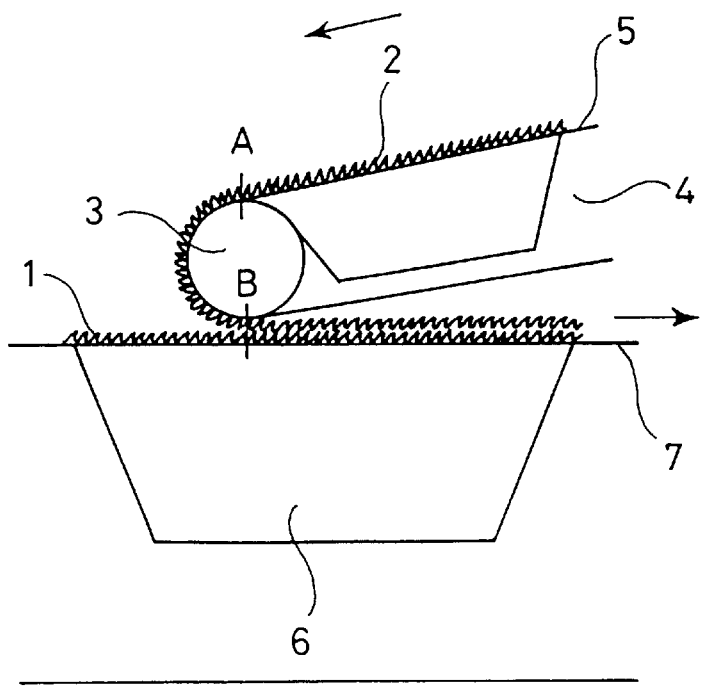
FIG. 5 shows a cross-sectional view of a preferred arrangement for formation of a second bulky layer.

In FIG. 5, a second bulky layer 2 is formed and laid down on top of a first bulky layer 1 and a support layer (not shown, but beneath the first bulky layer 1), the first bulky layer 1 and the support layer being preferably produced as part of a single in-line process as described herein. In this process, the second bulky layer 2 is formed in opposite orientation compared to the direction of movement of the first bulky layer 1. A suction box 4 is located beneath the air-permeable conveyor belt 5 on which the second bulky layer 2 is transported and helps to maintain the structure of the fibrous web forming the second bulky layer 2. In order to maintain the structure of the second bulky layer 2 and to improve cohesion and bonding between the first bulky layer 1 and the second bulky layer 2, a perforated suction roll 3 is used, so that a suction effect is obtained in the area where the conveyor belt 5 is adjacent to the suction roll 3. This allows the structure of the second bulky layer 2 to be maintained against the porous conveyor belt 5 during the change of direction that occurs between point A and point B. Under these conditions, no draft is exerted on the second bulky layer 2. At point B the bulky layer is released from conveyor belt 5 and is laid down, by means of a suction box 6, on top of the first bulky layer 1 (which is maintained by the suction action of the suction box 6 against the porous conveyor belt 7). By means of this arrangement, draft during the transfer of the second bulky layer 2 from the conveyor belt 5 to the conveyor belt 7 is very low, i.e. less than about 5%.

The upper side of bulky layer 2 (i.e. "upper" when bulky layer 2 is still located on the conveyor belt 5) is slightly uneven, since some of the fibres are vertically oriented. The lower side, on the other hand, is more smooth, because the fibres are laying against the conveyor belt 5. For bulky layer 1 the situation is the same. As a result of the fact that bulky layer 2 is formed in opposite orientation compared to bulky layer 1, the uneven surface of bulky layer 2 is in contact with the upper uneven surface of bulky layer 1 when bulky layer 2 is laid down on bulky layer 1. This provides an additional advantage in that cohesion and bonding between bulky layer 2 and bulky layer 1 are improved.

Figure 6:
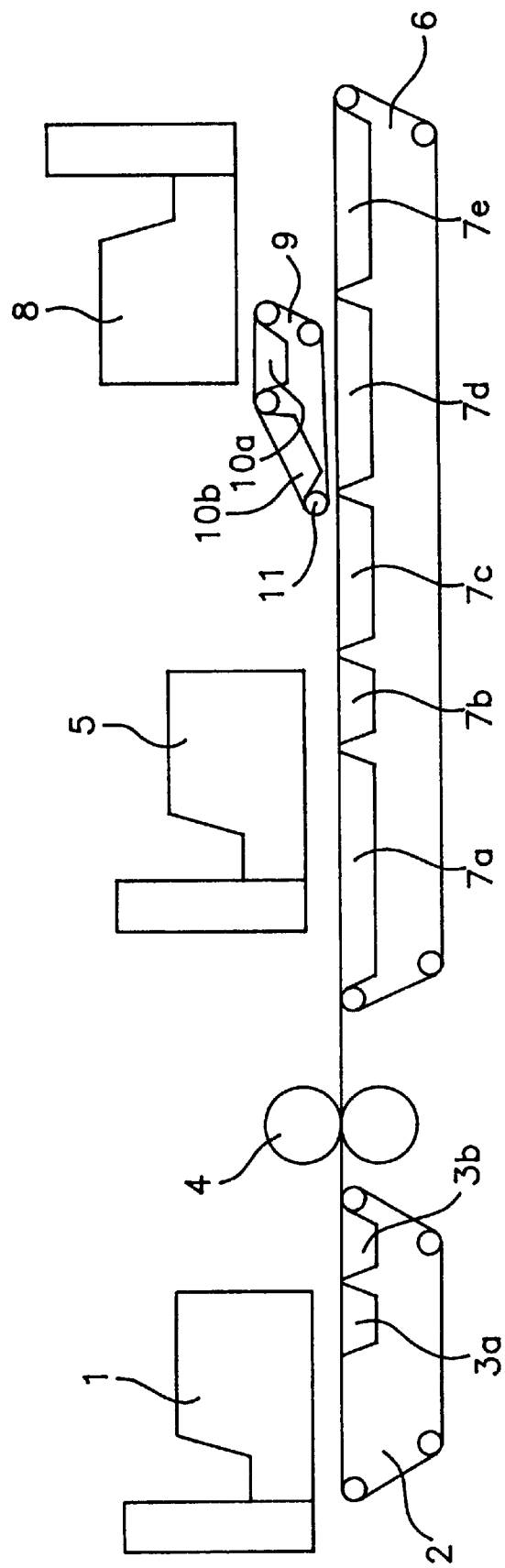
FIG. 6 shows schematically a production line for the in-line production of composite nonwovens according to the invention comprising a support layer and two bulky layers.

In FIG. 6 a support layer is produced by means of a first card 1 and a first webformer 2 which includes first suction boxes 3a and 3b. (As mentioned above, the support layer may alternatively be produced in other ways, e.g. by spunbonding). The first card 1 and suction box 3a function as described above with reference to FIG. 2, i.e. the fibrous web produced by card 1 is laid down on the porous conveyor belt of the webformer 2 with the aid of laydown suction box 3a, and the structure of the fibrous web is maintained as the web travels along the conveyor belt by means of holddown suction box 3b. The fibrous web forming the first support layer is subsequently consolidated by means of a thermobonding calender 4, which preferably is of the type described with reference to FIG. 4.

After consolidation of the support layer in the calender 4, a first bulky layer is produced by means of card 5, and the first bulky layer is laid down on top of the support layer, which now is travelling along the porous conveyor belt of webformer 6. Webformer 6 similarly uses a series of suction boxes 7a–7e to hold the support layer, the first bulky layer and (when formed; see below) the second bulky layer onto the conveyor belt to avoid modification of the web structure. Suction box 7b is a laydown suction box for the first bulky layer produced by card 5.

Finally, a second bulky layer is formed by means of card 8 and is laid down on webformer 9, which comprises a porous conveyor belt together with suction boxes 10a and 10b as well as a perforated suction roll 11, i.e. the second bulky layer is formed and laid down on the first bulky layer as described above with reference to FIG. 5. The combination of the support layer, the first bulky layer and the second bulky layer are subsequently subjected to bonding, e.g. by means of a through-air bonding oven (not shown).

The area subject to suction as well as the strength of the vacuum generated by each of the various suction boxes 3a–3b, 7a–7e and 10a–10b as well as the suction roll 11 can of course be varied according to process parameters such as the production speed, type of fibres, whether the suction is for laydown or holddown purposes, etc.

EXAMPLES

The composite nonwovens described in Examples 1–10 below were produced on a pilot line, the general procedure for production of the various nonwovens being, except where otherwise noted, as follows:

The first step is formation of the support layer, which is performed by carding, followed by consolidation of the support layer, which is performed by calender bonding. The first and second bulky layers are formed separately in a card, the fibres present in each bulky layer being homogeneously blended prior to carding. After consolidation of the support layer, the first bulky layer is laid down on the support layer, whereafter the second bulky layer is laid down on top of the first bulky layer. The composite construction consisting of, in most cases, these three layers, then passes through a through-air bonding oven, where the binder fibres in the bulky layers provide bonds both between the fibres within the individual bulky layers and between the layers, i.e. between the first bulky layer and the support layer as well as between the first bulky layer and the second bulky layer. Thermobonding was generally at a temperature of 135–145° C., depending on the fibre type, dtex and line speed.

The nonwovens of the subsequent Examples A–I were produced on a commercial line using the process described above. In this case, the different layers are formed at the same time on three separate cards, the first card forming and consolidating (calender bonding) the support layer. The first bulky layer is formed and laid on top of the support layer, and the second bulky layer is then formed (using a card in opposite orientation to the first and second cards) and laid on top of the first bulky layer, whereafter all three layers are transported to the bonding oven where the bonding of the bulky layers is performed (i.e. bonding within the bulky layers, between the bulky layers and between the bulky layers and the support layer).

Test methods

In the tests described below, the test liquid used was a 0.9% NaCl solution.

3×strike-through test

This is a modified EDANA method based on EDANA standard No. ERT 150.2-93. The modification in relation to the standard method is that the strike-through measurement is performed three times on precisely the same spot on the nonwoven. The underlying absorbent pad (filter paper) is replaced after each of the individual strike-through runs. The nonwoven is not dried or wiped off in any way between runs. Three sequences (each with three runs) are conducted, and the mean and standard deviation of the measurements are calculated for each run. In this test, the third strike-through time is preferably at the most about 2.5 sec, more preferably at the most about 2.0 sec, more preferably at the most about 1.5 sec, and most preferably at the most about 1.0 sec.

Rewet test (EDANA)

The rewet of the nonwovens is determined in accordance with EDANA standard No. ERT 151.0-93. The results, expressed in g, are the average of three individual measurements. This test measures the ability of a nonwoven to act as a barrier against the transport of liquid from a nearly saturated absorbing material to a dry absorbing material. The absorbing material under the nonwoven is 85% saturated with a liquid, and after a compression time of 3 min., a piece of filter paper is placed on top of the nonwoven and a weight is placed on top of the filter paper. After 2 min. the weight is removed and the weight gain of the filter paper is recorded. In this test, the rewet, i.e. weight gain of the filter paper, is preferably at the most 0.20 g, more preferably at the most about 0.15 g, more preferably at the most about 0.10 g, e.g. no more than about 0.08 g.

Retention test

The retention of a nonwoven is determined in accordance with EDANA standard No. ERT 10.1-72 (part 2). The results, expressed in %, are the average of five individual measurements. The test measures the ability of a material to retain liquid, the liquid retention capacity being the amount of liquid stored within the nonwoven specimen during a given time period (3 min).

Demand absorbency

This test measures the ability of a nonwoven sample to absorb liquid over a time span, the sample being placed on a perforated plate from which liquid is absorbed over the given time period; the liquid is not in any way pumped up or submitted to pressure. A nonwoven sample (10×10 cm) is placed on a coverstock on top of a perforated plate from which liquid has access from below. 3 pieces of filter paper (9×9 cm) are placed on top of the sample (ref: Whatmann no. 3) and on top of this a circular weight (45 g; diameter 9 cm) is placed in order to ensure contact between the different layers. As the sample takes up liquid, the weight gain is measured and recorded by a computer for further analysis, the measurement being made at predetermined intervals in the time span of t=0 sec to t=180 sec. The result measured at 180 sec is the total liquid absorbency capacity. The uptake during the first 15 sec. can be subjected to a linear regression analysis to determine the liquid absorbency speed. The absorbency is expressed as weight gain in g (g liquid absorbed).

Measuring the absorbency in this manner, so that the liquid must flow in the opposite direction of gravity, shows the nonwoven's ability to acquire and absorb liquid in a "worst case" scenario. For a good nonwoven of the distribution type, the demand absorbency at 5 sec should be as high as possible and is preferably at least about 7.0 g, more preferably at least about 7.5 g, still more preferably at least about 8.0 g.

Acquisition/distribution test

This test method measures a nonwoven product's ability to acquire and distribute an instantaneously added quantity of liquid. A nonwoven sample (100×280 mm) is placed on top of 10 pieces of filter paper (ref: Whatmann no. 3 or Eaton-Dikeman) on a support (as an alternative, an absorbent core with a known density and percentage of superabsorbent polymer can be used instead of filter paper). A plexiglas plate with a weight of 3.5 kg and a hole with a diameter of 5 cm is placed on top of the nonwoven sample. 60 ml of test liquid is poured onto the nonwoven sample through the hole in the plexiglass plate at t=0. The time required for the sample to acquire and absorb the liquid is measured. This procedure is repeated at 20 min intervals with the same filter paper/absorbent core a total of 3 times on the same sample in order to obtain an expression for the efficiency of the product to acquire liquid after several mictions. The result (sec) is the average of 3 repetitions.

ADD test (Acquisition/distribution/dryness)

The objective of this test is to measure the acquisition time and wetback for a composite nonwoven (or a baby diaper containing the nonwoven) subjected to 3 insults of synthetic urine. The nonwoven is positioned on a foam cushion simulating a human body. The cushion is inclined at an angle of 30° to give an insult point orientation similar to that of a baby in a sitting position. Pressure applied on the whole surface of the nonwoven is constant and homogeneous during the test.

The test uses the following equipment: a cushion, a dispensing pump with controlled flowrate, a stopwatch/timer, a weight of 4 kg (63.5 g/cm$^2$—100×100 mm), an acrylic plate with an acrylic ring (inner diameter 80 mm, total weight 2.5 kg), an acrylic core (to seal the acrylic inner diameter ring and maintain a homogeneous pressure on the surface of the diaper; acrylic ring height=acrylic core height), synthetic urine (surface tension: 70 mN/m±2) made of 0.9% NaCl saline solution, 3×5 pieces of filter paper Whatman N°3 (70×90 mm), a balance (accuracy 0.01 g).

Test parameters: nonwoven composite size: 100×280 mm; 3×60 ml synthetic urine; pump flow=1256 ml/min to saturate the insult area; the weight of 4 kg simulates the pressure on the diaper of a baby in a sitting position; time between insults 20 min; time for wetback 3 min. The dry weight of each stack of 5 filter papers is recorded in order to later calculate the wetback (P1 of each stack).

Procedure: The composite nonwoven, with the bulky side up and placed on top of 3 absorbent cores of the same size as the nonwoven sample, is fixed on the cushion with pins. The acrylic plate is put on top of the nonwoven with the ring centered at the insult point. The pump and the stopwatch are started (1 insult=60 ml) simultaneously. The stopwatch is stopped when the synthetic urine is fully absorbed (T1). The acrylic ring is sealed with the acrylic core. The procedure is repeated twice at 20 min intervals. After the third insult the composite nonwoven is removed from the cushion (care is taken to maintain the diaper in a horizontal, straight position) and placed on a stainless steel plate. A stack of 5 filter papers is placed under the weight at the insult point of the nonwoven for 3 min, the stack of 5 filter papers is weighed and the wetback value (P2) is noted.

Calculations:

Total acquisition time, T=T1+T2+T3;

Wetback=Wetback after insult No. 3=P2−P1.

The acquisition time (third insult, i.e. T3), should be at the most about 60 sec, preferably at the most about 50 sec, more preferably at the most about 40 sec, more preferably at the most about 30 sec, more preferably at the most about 25 sec, most preferably at the most about 20 sec. The wetback should be at the most about 8 g, typically at the most about 7 g, preferably at the most about 5 g, more preferably at the most about 4 g, more preferably at the most about 3 g, most preferably at the most about 2 g.

The nonwovens prepared in Examples 1–10 are described below and are in addition summarized in the appended tables.

EXAMPLE 1

Support layer: basis weight about 15 g/m$^2$; 100% PP (polypropylene) fibres, 1.7 dtex, length 38–44 mm, treated with a permanent hydrophilic finish (HY-REPEAT fibres from Danaklon a/s).

Bulky layer: basis weight about 30 g/m$^2$; 80% PET (polyethylene terephthalate) fibres, 6.7 dtex (available from Hoechst Celanese), length 50–60 mm; 20% bicomponent sheath-core PP/PE (polypropylene/polyethylene) binder fibres, 1.7 dtex, treated with a permanent hydrophilic finish (ES-REPEAT-C from Danaklon a/s).

Example 1a: The single bulky layer was laid down on the support layer and this construction was subsequently passed through a through-air bonding oven.

Example 1b (comparative example): The single bulky layer was first passed through a through-air bonding oven and subsequently laid down on the support layer.

EXAMPLE 2

Support layer: basis weight about 12 g/m$^2$; 100% PP fibres, 1.7 dtex, 38–44 mm, treated with a permanent hydrophilic finish (HY-REPEAT fibres from Danaklon a/s).

First bulky layer: basis weight about 12 g/m$^2$; 80% PET fibres, 7 dtex; 20% bicomponent PP/PE binder fibres, 1.7 dtex, treated with a permanent hydrophilic finish (ES-REPEAT-C from Danaklon a/s).

Second bulky layer: basis weight about 23 g/m$^2$; 80% PET fibres, 6.7 dtex; 20% bicomponent PP/PE binder fibres, 1.7 dtex, treated with a permanent hydrophilic finish (ES-REPEAT-C fibres available from Danaklon a/s).

EXAMPLE 3

Support layer: basis weight about 15 g/m$^2$; 100% PP fibres, 1.7 dtex, 38–44 mm, treated with a permanent hydrophilic finish (HY-REPEAT fibres from Danaklon a/s).

First bulky layer: basis weight about 12 g/m$^2$; 80% (Example 3a: 75%) PET fibres, 1.7 dtex; 20% (Example 3a: 25%) bicomponent binder fibres as listed below.

Second bulky layer: basis weight about 23 g/m$^2$: 80% PET fibres, 6 dtex; 20% bicomponent fibres as listed below.

Binder fibres in first and second bulky layers:

Example 3a: PP/PE bicomponent fibre, 1.7 dtex, treated with a permanent hydrophilic finish (ES-REPEAT-C available from Danaklon a/s).

Example 3b: PET/PE bicomponent fibre; 5.3 dtex (available from Wellman).

Example 3c: PP homopolymer monocomponent fibres with a broad bonding window, 1.7 dtex (available from Danaklon a/s).

EXAMPLE 4

In this example, only different bulky layers were produced (i.e. no support layer or second bulky layer), in order to illustrate the function of the bulky layer when produced with different types of fibres. Each bulky layer had a basis weight of about 17.5 g/m$^2$ and comprised 20% bicomponent binder PP/PE fibres of 1.7 dtex (non-permanent hydrophilic finish, available from Danaklon a/s) together with 80% of:

a) PET solid fibres of about 1.7 dtex, bidimensional crimp,
b) PET solid fibres of about 3.3 dtex, bidimensional crimp,
c) PET solid fibres of about 6.7 dtex, bidimensional crimp,
d) PET hollow fibres of about 6.0 dtex, bidimensional crimp,
e) PET solid fibres of about 6.7 dtex and having a spiral, three-dimensional crimp.

Each bulky layer was bonded in a through-air bonding oven.

EXAMPLE 5

Support layer: basis weight about 15 g/m$^2$; 100% PP fibres, 1.7 dtex, 38–44 mm. The fibres of the support layer were treated as listed below.

First bulky layer: basis weight about 12 g/m$^2$; 80% (Example 5a: 75%) PET fibres, 1.7 dtex; 20% (Example 5a: 25%) bicomponent PP/PE binder fibres, 1.7 dtex. The binder fibres were treated as listed below.

Second bulky layer: basis weight about 20 g/m$^2$; 80% PET hollow fibres, 6 dtex; 20% bicomponent PP/PE binder fibres of the same type as in the first bulky layer.

The fibres of the support layer and the binder fibres of the first and second bulky layers were treated as follows:

Example 5a: Support layer fibres treated with a permanent hydrophilic finish (HY-REPEAT fibres available from Danaklon a/s); binder fibres treated with a permanent hydrophilic finish (ES-REPEAT-C fibres available from Danaklon a/s).

Example 5b: Support layer fibres treated with a non-permanent hydrophilic finish (SOFT 71 fibres available from Danaklon a/s); binder fibres treated with a permanent hydrophilic finish (ES-REPEAT-C fibres available from Danaklon a/s).

Example 5c: Support layer fibres treated with a permanent hydrophilic finish (HY-REPEAT fibres available from Danaklon a/s); binder fibres treated with a non-permanent hydrophilic finish (ES-C-PHILIC fibres available from Danaklon a/s).

Example 5d: Example 5c: Support layer fibres treated with a non-permanent hydrophilic finish (SOFT 71 fibres available from Danaklon a/s); binder fibres treated with a non-permanent hydrophilic finish (ES-C-PHILIC fibres available from Danaklon a/s).

EXAMPLE 6

Support layer: basis weight about 15 g/m$^2$; 100% PP fibres, 2.2 dtex, 38–44 mm, treated with a permanent hydrophilic finish (HY-REPEAT fibres from Danaklon a/s).

First bulky layer: basis weight about 15 g/m$^2$; 80% PET hollow fibres, 6 dtex; 20% bicomponent PP/PE binder fibres, 1.7 dtex, treated with a permanent hydrophilic finish (ES-REPEAT-C from Danaklon a/s).

Second bulky layer: basis weight about 15 g/m$^2$; 80% PET hollow fibres, 6 dtex; 20% bicomponent PP/PE binder fibres, 1.7 dtex, treated with a permanent hydrophilic finish (ES-REPEAT-C fibres available from Danaklon a/s).

EXAMPLE 7

Support layer: basis weight about 15 g/m$^2$; 100% PP fibres, 1.7 dtex, 38–44 mm, treated with a permanent hydrophilic finish (HY-REPEAT fibres from Danaklon a/s).

First bulky layer: basis weight about 20 g/m$^2$; 80% PET hollow fibres, 6 dtex; 20% bicomponent PP/PE binder fibres, 1.7 dtex, treated with a permanent hydrophilic finish (ES-REPEAT-C from Danaklon a/s).

Second bulky layer: basis weight about 12 g/m$^2$; 75% PET fibres, 1.7 dtex; 25% bicomponent PP/PE binder fibres, 1.7 dtex, treated with a permanent hydrophilic finish (ES-REPEAT-C fibres available from Danaklon a/s).

EXAMPLE 8

Support layer: basis weight about 15 g/m$^2$; 100% PP fibres, 1.7 dtex, 38–44 mm, treated with a permanent hydrophilic finish (HY-REPEAT fibres from Danaklon a/s).

First bulky layer: basis weight about 20 g/m$^2$; 80% PET hollow fibres, 6 dtex; 20% bicomponent PP/PE binder fibres, 1.7 dtex, treated with a permanent hydrophilic finish (ES-REPEAT-C from Danaklon a/s).

Second bulky layer: basis weight about 12 g/m$^2$; 100% bicomponent PP/PE binder fibres, 1.7 dtex, treated with a permanent hydrophilic finish (ES-REPEAT-C fibres available from Danaklon a/s).

EXAMPLE 9

Support layer: basis weight about 15 g/m$^2$; 100% PP fibres, 1.7 dtex, 38–44 mm, treated with a permanent hydrophilic finish (HY-REPEAT fibres from Danaklon a/s).

First bulky layer: basis weight about 12 g/m$^2$; 100% bicomponent PP/PE binder fibres, 1.7 dtex, treated with a permanent hydrophilic finish (ES-REPEAT-C from Danaklon a/s).

Second bulky layer: basis weight about 20 g/m$^2$; 80% PET hollow fibres, 6 dtex; 20% bicomponent PP/PE binder fibres, 1.7 dtex, treated with a permanent hydrophilic finish (ES-REPEAT-C fibres available from Danaklon a/s).

EXAMPLE 10

Support layer: basis weight about 15 g/m$^2$; 100% PP fibres, 1.7 dtex, 38–44 mm, treated with a permanent hydrophilic finish (HY-REPEAT fibres from Danaklon a/s).

First and second bulky layers: basis weight (each) about 17.5 g/m$^2$; 80% PET fibres, 3.3 dtex; 20% bicomponent PP/PE binder fibres, 1.7 dtex, treated with a permanent hydrophilic finish (ES-REPEAT-C from Danaklon a/s).

Test results for Examples 1–10

The nonwovens of the examples were subjected to various tests using the test methods described above. The tables below summarize the composition of the various nonwovens and the results of tests performed on the nonwovens of Examples 1–10:

| | Suppoer layer | | | | 1st bulky layer | | | | 2nd bulky layer | | | |
|---|---|---|---|---|---|---|---|---|---|---|---|---|
| Ex. | wt. g/m$^2$ | type | dtex | perm. hydrophilic | wt. g/m$^2$ | type | dtex | perm. hydrophilic | g/m$^2$ | type | dtex | hydrophilic |
| 1a+ | 15 | PP | 1.7 | yes | 30 | 80% PET | 6.7 | — | — | — | — | — |
| 1b | | | | | | 20% PP/PE | 1.7 | yes | | | | |
| 2 | 12 | PP | 1.7 | yes | 12 | 80% PET | 7 | — | 23 | 80% PET | 6.7 | — |
| | | | | | | 20% PP/PE | 1.7 | yes | | 20% PP/PE | 1.7 | yes |
| 3a | 15 | PP | 1.7 | yes | 12 | 75% PET | 1.7 | — | 20 | 80% PEThollow | 6 | — |
| | | | | | | 25% PP/PE | 1.7 | yes | | 20% PP/PE | 1.7 | yes |
| 3b | 15 | PP | 1.7 | yes | 12 | 80% PET | 1.7 | — | | 80% PEThollow | 6 | — |
| | | | | | | 20% PET/PE | 5.3 | | | 20% PET/PE | 5.3 | yes |
| 3c | 15 | PP | 1.7 | yes | 12 | 80% PET | 1.7 | — | | 80% PEThollow | 6 | — |
| | | | | | | 20% PP | 1.7 | yes | | 20% PP | 1.7 | yes |
| 4 | — | — | — | — | 17.5 | 20% PP/PE | 1.7 | no | — | — | — | — |
| 4a | — | — | — | — | | 80% PET | 1.7 | — | — | — | — | — |
| 4b | — | — | — | — | | 80% PET | 3.3 | — | — | — | — | — |
| 4c | — | — | — | — | | 80% PET | 6.7 | — | — | — | — | — |
| 4d | — | — | — | — | | 80% PEThollow | 6.0 | — | — | — | — | — |
| 4e | — | — | — | — | | 80% PEThollow 3D-crimp | 6.7 | — | — | — | — | — |
| 5a | 15 | PP | 1.7 | yes | 12 | 75% PET | 1.7 | — | 20 | 80% PEThollow | 6 | — |
| | | | | | | 25% PP/PE | 1.7 | yes | | 20% PP/PE | 1.7 | yes |
| 5b | 15 | PP | 1.7 | no | | 80% PET | 1.7 | — | | 80% PEThollow | 6 | — |
| | | | | | | 20% PP/PE | 1.7 | yes | | 20% PP/PE | 1.7 | yes |
| 5c | 15 | PP | 1.7 | yes | | 80% PET | 1.7 | — | | 80% PEThollow | 6 | — |
| | | | | | | 20% PP/PE | 1.7 | no | | 20% PP/PE | 1.7 | no |
| 5d | 15 | PP | 1.7 | no | | 80% PET | 1.7 | — | | 80% PEThollow | 6 | — |
| | | | | | | 20% PP/PE | 1.7 | no | | 20% PP/PE | 1.7 | no |
| 6 | 15 | PP | 2.2 | yes | 15 | 80% PEThollow | 6 | — | 15 | 80% PEThollow | 6 | — |
| | | | | | | 20% PP/PE | 1.7 | yes | | 20% PP/PE | 1.7 | yes |
| 7 | 15 | PP | 1.7 | yes | 20 | 80% PEThollow | 6 | — | 12 | 75% PET | 1.7 | — |
| | | | | | | 20% PP/PE | 1.7 | yes | | 25% PP/PE | 1.7 | yes |
| 8 | 15 | PP | 1.7 | yes | 20 | 80% PEThollow | 6 | — | 12 | PP/PE | 1.7 | yes |
| | | | | | | 20% PP/PE | 1.7 | yes | | | | |
| 9 | 15 | PP | 1.7 | yes | 12 | PP/PE | 1.7 | yes | 20 | 80% PEThollow | 6 | — |
| | | | | | | | | | | 20% PP/PE | 1.7 | yes |
| 10 | 15 | PP | 1.7 | yes | 17.5 | 80% PET | 3.3 | — | 17.5 | 80% PET | 3.3 | — |
| | | | | | | 20% PP/PE | 1.7 | yes | | 20% PP/PE | 1.7 | yes |

| | 3 times strike through | | | Rewet g | Retention % | Demand Absorbency | | Acquisition/Distribution test | | |
|---|---|---|---|---|---|---|---|---|---|---|
| Example | 1. str. sec. | 2 str sec. | 3 str. sec. | | | D.A. 5 sec g/g | D.A. 180 s g/g | 1. A/D | 2. A/D | 3. A/D |
| 1a | 1,7 | 1,66 | 1,76 | 0,07 | 606 | 6,2 | 20,46 | | | |
| 1b | 2,15 | 2,45 | 2,38 | 0,09 | | | | | | |
| 2 | 0,95 | 0,95 | 0,95 | 0,08 | 580 | 4,33 | 22,01 | 4,7 | 4,6 | 5,3 |
| 3a | 1,21 | 1,28 | 1,12 | 0,08 | 851 | 5,56 | 21,54 | 4,5 | 4,4 | 6,3 |
| 3b | 0,89 | 1,1 | 0,82 | 0,09 | 1036 | | | | | |
| 3c | 1,11 | 1,61 | 14,84 | 0,09 | 1221 | | | | | |
| 4a | 2,34 | | | 0,16 | 2070 | 7,06 | 22,02 | | | |
| 4b | 2,32 | | | 0,15 | 1352 | 6,57 | 24,19 | | | |
| 4c | 1,85 | | | 0,19 | 882 | 7,91 | 23,54 | | | |
| 4d | 1,7 | | | 0,17 | 1129 | 6,49 | 20,54 | | | |

-continued

| Example | 3 times strike through | | | Rewet g | Retention % | Demand Absorbency | | Acquisition/Distribution test | | |
|---|---|---|---|---|---|---|---|---|---|---|
| | 1. str. sec. | 2 str sec. | 3 str. sec. | | | D.A. 5 sec g/g | D.A. 180 s g/g | 1. A/D | 2. A/D | 3. A/D |
| 4e | 2,21 | | | 0,27 | 779 | 6,41 | 19,94 | | | |
| 5a | 1,21 | 1,28 | 1,12 | 0,08 | 851 | 5,56 | 21,54 | | | |
| 5b | 1,17 | 1,8 | 1,84 | 0,07 | 1069 | | | | | |
| 5c | 1,19 | 2,28 | 3,58 | 0,07 | 1313 | | | | | |
| 5d | 1,79 | 2,27 | 4,02 | 0,09 | 1195 | | | | | |
| 6 | 0,84 | 0,87 | 0,85 | 0,08 | 615 | 4,1 | 19,3 | 4,8 | 4,4 | 4,9 |
| 7 | 1,07 | 1,39 | 1,7 | 0,09 | 732 | | | | | |
| 8 | 1,25 | 1,32 | 1,42 | 0,08 | | | | | | |
| 9 | 1,23 | 1,25 | 1,35 | 0,07 | 1356 | 6,52 | 20,53 | | | |
| 10 | 1,63 | 1,6 | 1,54 | 0,07 | 1190 | 7,53 | 19,2 | 5,8 | 5,7 | 7,5 |

Comments on the results—Examples 1–10

EXAMPLE 1

This example shows firstly that satisfactory results can be achieved with only a single bulky layer (1a), and secondly that the strike-through time is poorer for the product (1b) in which the coverstock (support layer) is not bonded to the bulky layer. In other words, good contact between the layers is important for liquid transfer, the bonding points between the layers facilitating good cohesion between the layers and thus faster liquid transfer.

EXAMPLE 3

This example compares different binder fibres, namely:

3a: bicomponent PP/PE fibres

3b: bicomponent PET/PE fibres

3c: monocomponent PP fibres.

The strike-through times show some differences when comparing the three different types of binder fibres. It is possible to use all three types, although differences are detected when comparing the results of repeated mictions. The somewhat stiffer polyester core of the PET/PE fibres of Example 3b gives a good open structure to the product, allowing for low strike-through times. Comparing the PP/PE bicomponent fibres with the PP monocomponent fibres, the bicomponent fibre gives a better bonding than the monocomponent fibre. As a result, the product prepared with the monocomponent fibres tended to collapse after the third miction, which disturbed the open structure of the bulky layers and gave a poorer liquid throughput, expressed as an increased third strike-through time. Such binder fibres are therefore less advantageous for use in absorbent products that are designed to be subjected to repeated mictions, e.g. baby diapers, but may be suitable for other products, e.g. for feminine care products, in which the amount of liquid is not as great.

EXAMPLE 4

Examples 4a, 4b and 4c show solid PET fibres with bidimensional crimp, the dtex being 1.7, 3.3 and 6.7, respectively. Pore size dimensions are important with respect to liquid flow through processes, the flow rates of a material being larger with larger dtex. Thus, a higher dtex gives a larger pore size, which in turn gives a higher flow rate and a better acquisition. On the other hand, a lower dtex gives a smaller pore size, which in turn gives a lower flow rate and allows for better distribution properties. The flow rate is detected by the strike-through, and it may be seen in the table that the strike-through time decreases with increasing dtex fibres.

Examples 4c and 4d compare solid and hollow fibres, respectively, with substantially the same dtex (6.7 and 6.0 respectively). The flow rates are essentially the same for the two materials. However, liquid retention is slightly higher using the hollow fibres, which may be explained by the fact that there is a certain capillary effect when using hollow fibres as compared to solid fibres.

Examples 4c and 4e compare solid fibres with the same dtex but with bidimensional and 3-dimensional (spiral) crimp, respectively. The use of fibres with a 3-dimensional crimp gives a total smaller amount of large pores and thus a lower flow rate than with bidimensional crimp fibres. Fibres with a spiral crimp are therefore less advantageous when high acquisition is desired. Liquid retention for the two types of fibres is essentially the same.

Figure 7:
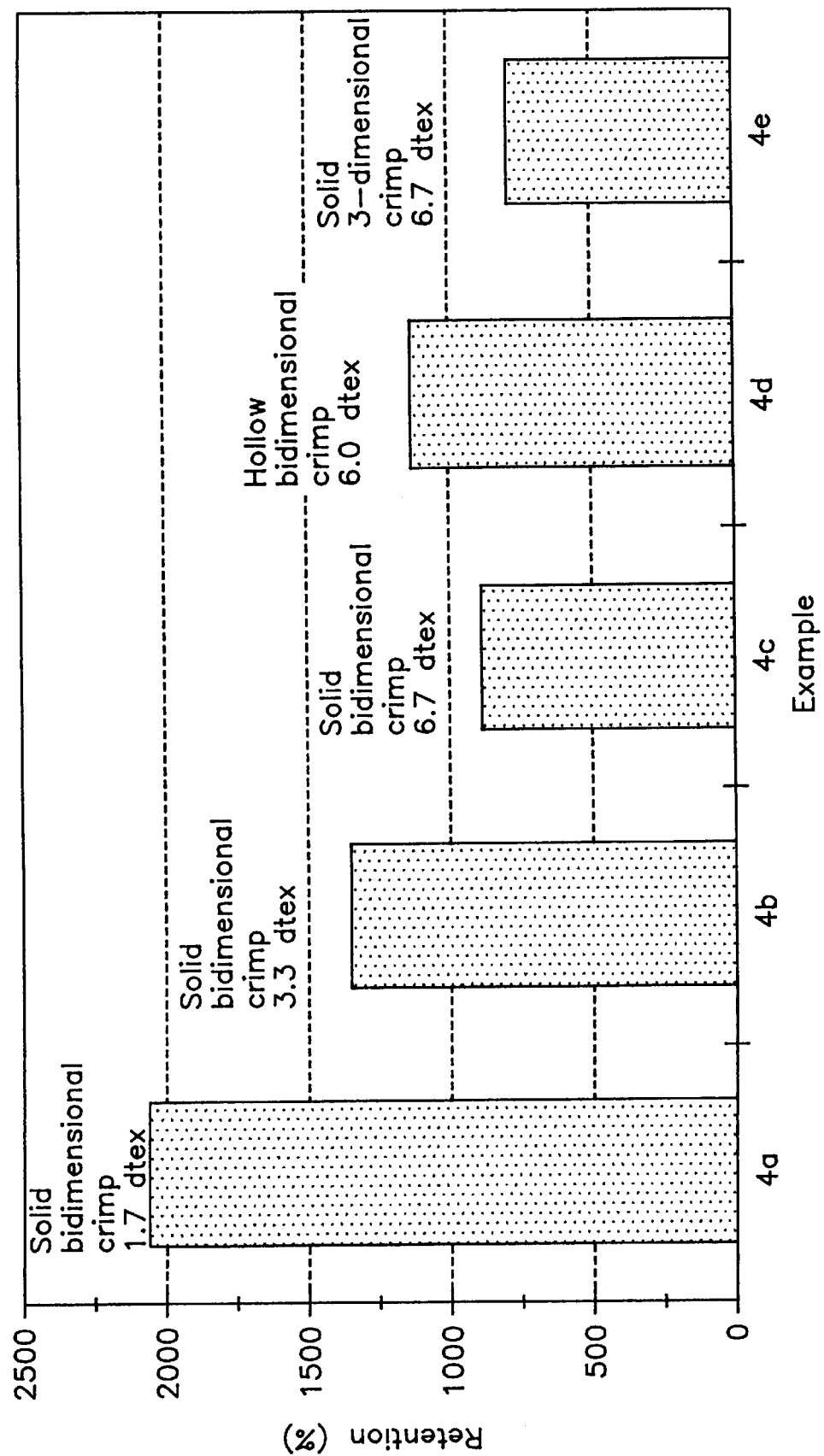
FIG. 7 shows the liquid retention results obtained for the composite nonwovens of Example 4a–4e.

The retention test results for Example 4a–4e are shown in FIG. 7.

Comparison of Examples 2, 3a, 6 and 10

These examples show the use of four different concepts:

Example 2: A mixture of 6.7 and 7 dtex PET fibres in the bulky layers gives a pure acquisition type. Retention is a little lower than with Example 6, since the fibres of Example 6 are hollow (hollow fibres providing some capillary effect in the form of very small pores and thus a higher retention). The strike-through time of these two concepts is approximately the same, and the acquisition time (acquisition/distribution test) is also approximately the same.

Example 6: Similar to Example 2, but with 6.0 dtex hollow PET fibres instead of the solid PET fibres of Example 2. This is an acquisition type with low retention and low strike-through time due to the high dtex, but also with a fair distribution (see demand absorbency results) due to the capillary effect of the hollow fibres.

Example 3a: The first bulky layer contains low (1.7) dtex PET fibres, giving a lower flow throughput and a higher retention, thus high distribution. The second (top) bulky layer contains high (6.0) dtex hollow PET fibres, giving a high flow throughput, a low strike-through and a low retention. The total construction is thus an acquisition-distribution (AD) type, since it first rapidly acquires liquid, which is then transferred to the next layer, which distributes the miction evenly, allowing for optimum utilization of the absorbent core.

Example 10: The first and second layers contain 3.3 dtex PET fibres, which means that the total pore volume is lower than that of Examples 2, 3a and 6. This concept is thus a distribution—distribution (DD) type, since the lower dtex gives a lower flow throughput, a higher retention and thereby a better distribution. Although the distribution is excellent, the acquisition time (strike-through) is slightly higher than that of the other examples (2, 3a and 6).

In all of these examples, rewet and also strike-through at the third miction are low. This is believed to be related to the permanent hydrophilic surface treatment of the binder fibres and of the support layer fibres.

The demand absorbency at 5 sec shows that the nonwovens' ability to absorb liquid over a small time span and is thus an expression for the absorption speed. In order to absorb quickly, the nonwoven must have the ability to distribute the liquid over a large area. Since the test sample has an area larger than the area exposed to liquid, a relatively larger uptake of liquid in the same time shows the ability to distribute liquid faster. When comparing the four concepts of Examples 2, 3a, 6 and 10, the demand absorbency at 5 sec varies by 46%, showing the difference between the acquisition and distribution types.

Demand absorbency at 180 sec shows the nonwovens' total absorbency capacity. High absorbency is a measure of good acquisition, i.e. the more liquid that can be absorbed, the more liquid that can be acquired. Demand absorbency at 180 sec varies by only 12% when comparing these four concepts.

These examples show that it is possible to obtain good transfer between layers and at the same time low rewet. This advantageous combination results from the fact that in the top bulky layer, good acquisition will be achieved (by means of high dtex fibres to give a large pore size and a high liquid throughput). The liquid retention in such a layer is low, however, so that good transfer to the next layer will occur. In the underlying bulky layer, liquid is distributed over the whole area or at least a substantial area of the product (due to a small pore size), allowing for high utilization of the absorbent core. Since the overall liquid retention within the multilayer structure is low, no liquid will be retained in it (i.e. all the liquid is effectively transferred to the core). The overall result is to allow for fast absorption (acquisition), good distribution and a very low rewet, thereby leaving the surface of the diaper dry.

The results of the acquisition/distribution test on these four concepts show the difference between using an acquisition type and a distribution type of liquid control system. Although the third acquisition time in general becomes slightly higher for a distribution type (Example 10), as compared to the other three concepts, the acquisition times are in all cases still very good. This is believed to be related in part to the use of fibres subjected to a permanent hydrophilic treatment.

Figure 9:
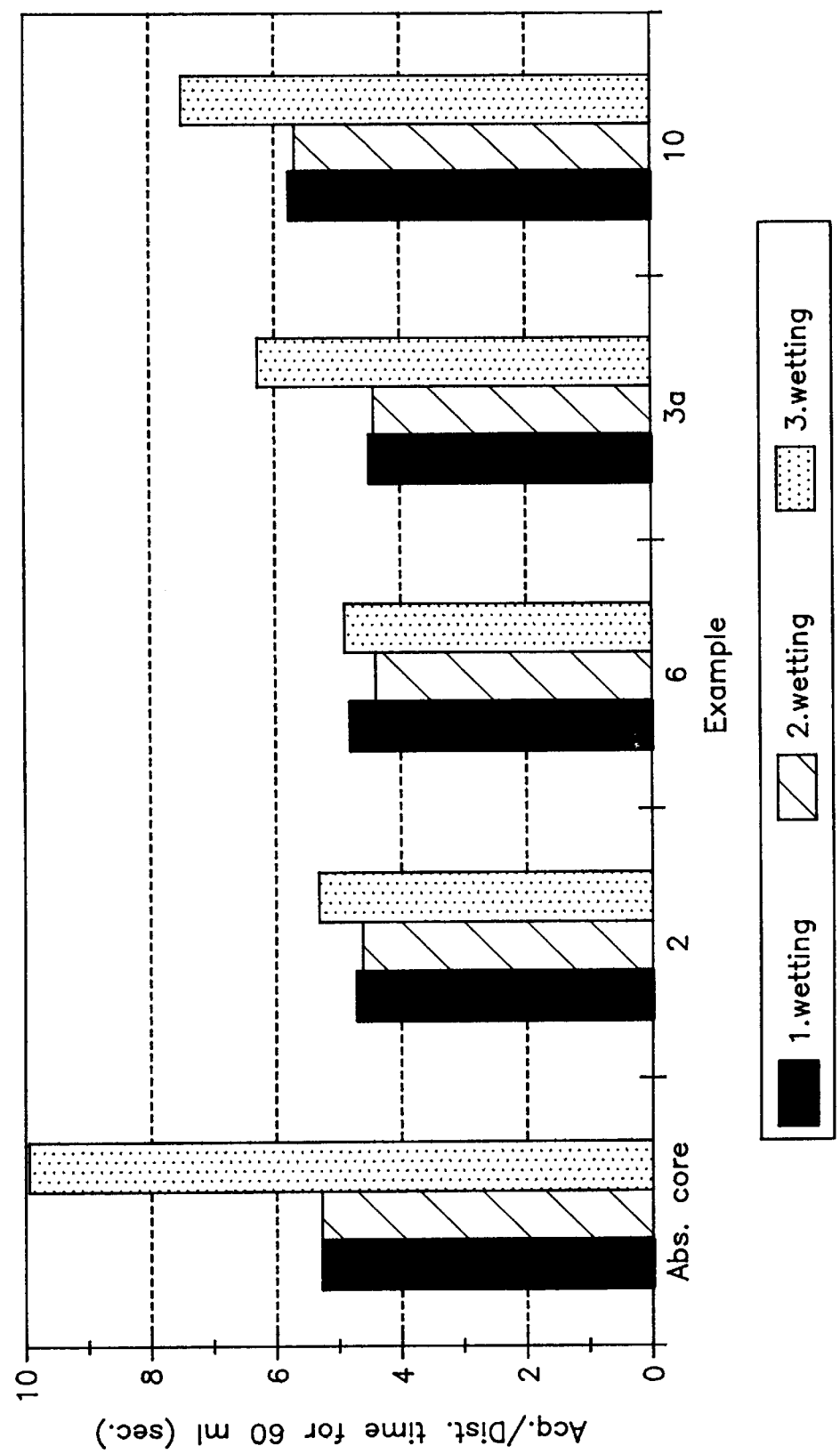
FIG. 9 shows the acquisition/distribution test results for Examples 2, 6, 4a and 10 as well as for an absorbent core.
Figure 10:
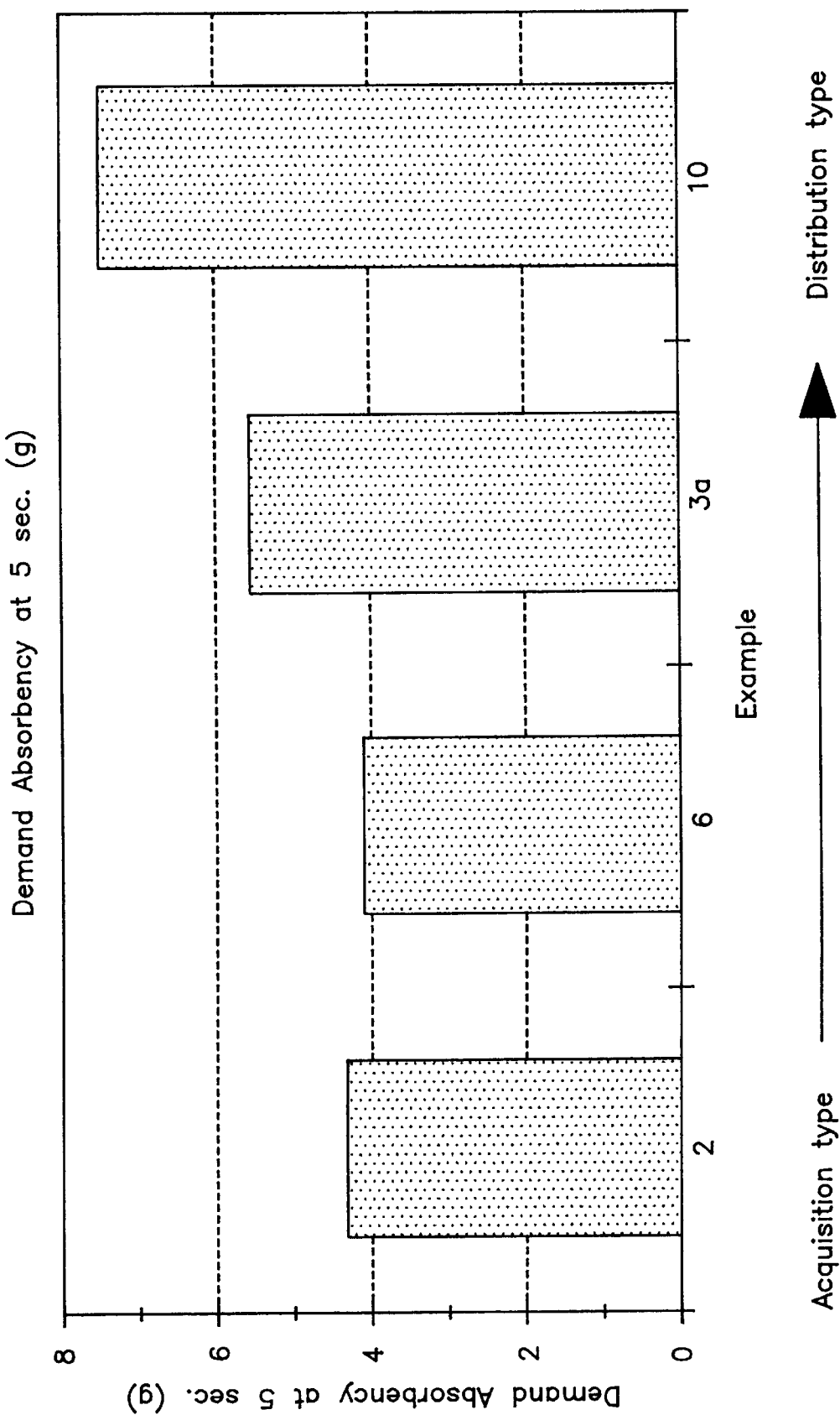
FIG. 10 shows the demand absorbency test results at 5 sec for Examples 2, 6, 3a and 10.

The acquisition/distribution test results for Examples 2, 6, 3a and 10 are shown graphically in FIG. 9 (which also shows test results for an absorbent core), and the demand absorbency test results are shown in FIG. 10.

Comparison of Examples 3a and 7

Example 3a contains, on top of the support layer, a first bulky layer based on 1.7 dtex solid PET fibres and a second bulky layer based on 6.0 dtex hollow PET fibres.

Example 7 shows a product in "reverse" order compared to Example 3a, i.e. with the support layer being on the opposite side of the bulky layers, but with the bulky layers having the same relationship to each other. In this example the support layer functions as a coverstock, and below the support layer is a first bulky layer based on 6.0 dtex hollow PET fibres and a second bulky layer based on 1.7 dtex solid PET fibres.

Both products are thus of the acquisition-distribution (AD) type, the difference between the two being the location of the support layer. The results for strike-through show that the reversed product with the support layer used as a coverstock (Example 7) has a strike-through time which is almost as low for that of the product of Example 3a.

Comparison of Examples 8 and 9

As is the case with Examples 3a and 7, Examples 8 and 9 also correspond to each other, but with the location of the support layer being reversed. Examples 8 and 9 are a different distribution type concept. In this case, the PP/PE bicomponent fibres are not as resilient as the PET fibres, which means that the product is slightly more dense and compact. The strike-through time in these two cases is therefore slightly higher, although still very good, and retention is high. Rewet is also very good (as is in fact the case for all the examples).

EXAMPLE 5

This example compares nonwovens produced from fibres treated in different ways in terms of a permanent or non-permanent hydrophilic finish:

|  | Support layer fibres | Bulky layer binder fibres |
| --- | --- | --- |
| 5a: | permanent | permanent |
| 5b: | non-permanent | permanent |
| 5c: | permanent | non-permanent |
| 5d: | non-permanent | non-permanent |

Figure 11:
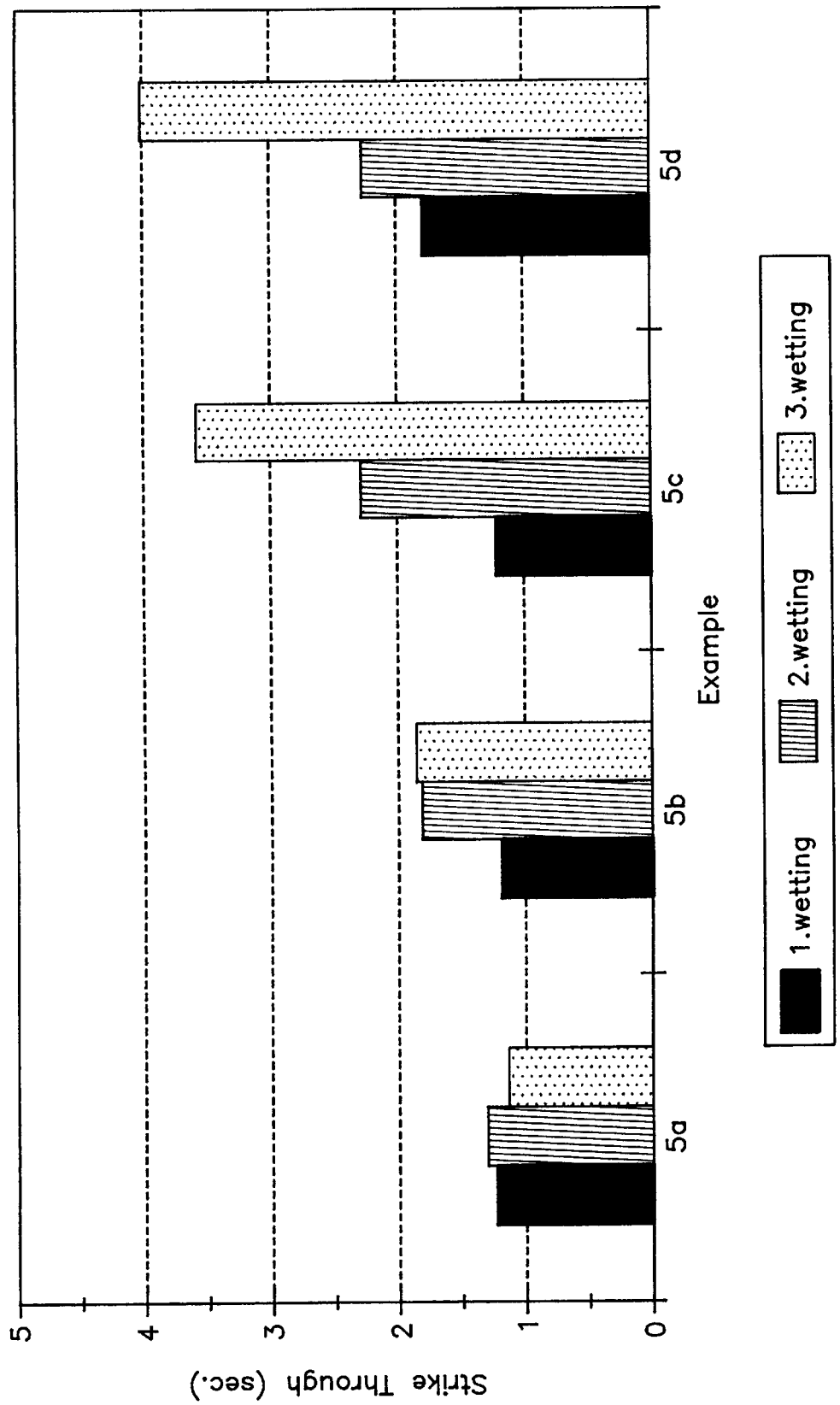
FIG. 11 shows the 3×strike-through test results for the nonwovens of Examples 5a–5d.

The results of the strike-through test for Example 5a–5e are shown graphically in FIG. 11, from which it is seen that the use of a permanent hydrophilic fibre treatment results in improved strike-through times. This is especially the case for the second and third strike-through times, which are significantly longer when the hydrophilic spin finish applied to the fibres is not permanent.

Retention test results for different concepts

Figure 8:
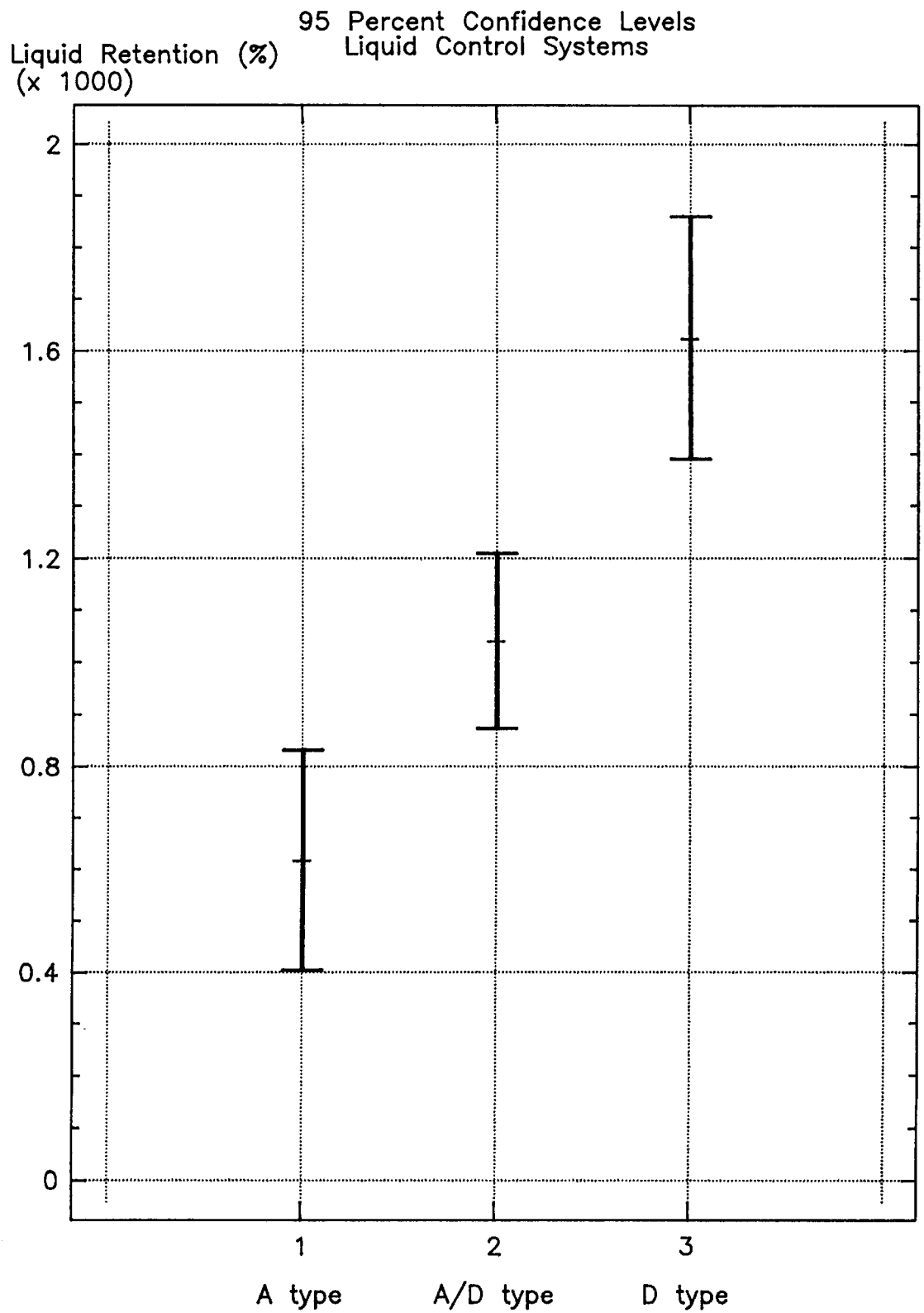
FIG. 8 shows 95% confidence intervals for the liquid retention of composite nonwovens of the acquisition (A), acquisition-distribution (A/D) and distribution (D) types.

As explained above, nonwovens prepared according to the present invention may be categorized in various groupings, including an acquisition (A) type, an acquisition-distribution (AD) type and a distribution (D) type. For the materials tested in the examples, a 95% confidence interval for retention for the A, AD and D type nonwovens was found to be as follows (shown graphically in FIG. 8):

A: 400–831; AD: 873–1205; D: 1390–1861

Although these results are actual test results for the samples tested, and therefore may vary for other samples, it is significant that the confidence intervals for the three different types, as characterized before the tests were performed, fall into three distinct and non-overlapping groups.

EXAMPLES A–I: DESCRIPTION AND RESULTS

The composition of the composite nonwovens produced according to Examples A–I as well as the test results for these nonwovens are given in the tables below. In the table containing the results, the following information is given: the basis weight of the composite nonwoven, the $1^{st}$ strike-through time with the support layer turned upwards, the strike-through time (in the "normal" position) for the $3^{rd}$ insult, the rewet, the retention, the demand absorbency at 5, 10 and 15 seconds as well as the maximum demand absorbency, the acquisition times T1, T2 and T3 from the ADD test, and the wetback value from the ADD test.

Among Examples A–I, only Example H uses permanently hydrophilic PF fibres in the support layer. The fineness of the support layer fibres in these examples is generally 3.3 dtex. The 3.3 dtex fibres give a more open structure than the finer fibres used in the support layer in Examples 1–10, thus allowing for good acquisition time. Although the acquisition time is improved when using a permanent hydrophilic fibre, the open structure of the support layer in these examples means that a permanent hydrophilic finish is not strictly necessary.

Examples A and B: These 2 examples show the effect of changing the base weight of the bulky layers. It can be seen that a reduction in base weight of approx. 17% in the bulky layers (from B to A) has a negative impact on the acquisition time. Also, the total absorbency is effected by this reduction in base weight, with less total liquid being absorbed. Both are related the fact that there are less fibres and thus a reduced numbers of pores to acquire and hold the liquid. The absorbency speeds, which are related to the distribution function, are equal, however. Due to the use of a permanent hydrophilic finish on the binder fibres, it has been possible to obtain a good distribution function even when using relatively high dtex (7.0 dtex) matrix fibres The liquid retention is in the range expected for a large pore size material.

Examples B and C: These examples once again demonstrate the effect of using hollow matrix fibres compared to solid fibres. The use of hollow fibres will, due to the good stability of the porous structure even under high volumes and rapid speed of the miction, give better results in terms of acquisition time. A further explanation of this is also the fact that the actual diameter of the fibre is higher than that of a solid fibre with the same dtex, allowing for a more open structure (larger pore sizes), which in turn results in increased liquid flow throughput. It may also be seen that the increased bulk stability allows for greatly improved wetback properties. An approximately 35% decrease in wetback is thus observed when using hollow matrix fibres compared to solid fibres.

Examples D and E: In these examples the dtex of the support layer has been decreased from 3.3 dtex to 2.2 dtex. One conceivable effect of this change could be that the liquid acquisition would be slowed down (higher acquisition time), as the pores of this structure would be smaller and thereby reduce the liquid throughput speed. However, in these examples the base weight of the second bulky layer has been increased to prevent this from happening, leaving the material with a very good acquisition time. Notice also that although the matrix fibre is a solid fibre of 7 dtex, the acquisition time is still very good and the rewet is low. This is believed to be due to the increased base weight and thus an increased void space.

Examples F and G: These examples illustrate a quite different structure compared to the above. The total base weight has been significantly reduced (to 30 and 26 gsm, respectively), but the acquisition time is equal to that of Example A, which has a base weight of 40 gsm. The use of hollow matrix fibres in the second bulky layer of these examples allows the liquid acquisition time to remain very good. The use of 100% bicomponent fibres in the first bulky layer results in excellent distribution properties, as the average pore size is reduced, thus allowing the liquid to wick better. This effects the rewet, however, as the bulkiness is reduced compared to Example B.

Examples H and B: These examples demonstrate the effect of using a permanent hydrophilic finish in the PP fibre of the support layer. The permanent hydrophilic finish shows its effect most clearly after repeated mictions. The hydrophilicity of the support layer (the transfer layer) in Example H is maintained even after several mictions, allowing the liquid to pass through uninhibited. Also, the wetback is significantly improved due the increased speed of liquid transfer to the absorbent core.

Examples I and F: These examples demonstrate the use of 100% PP fibres in the first bulky layer (Example I) compared to using 100% PP/PE bicomponent fibres in the first bulky layer (Example F). Results similar to those of Example F can thus be obtained when using PP fibres in the first bulky layer.

The composite nonwoven materials show excellent strike-though times when the support layer is used as a coverstock layer. This can be seen e.g. by comparing the results for Examples E and D. D is equivalent to E, but E has been turned upside down, i.e. the support layer of E is used as a coverstock.

| | | | | | |
|---|---|---|---|---|---|
| | | | Example A | | |
| Support Layer | | Bulky Layer N° 1 | | Bulky Layer N° 2 | |
| Basis weight | 15 g/m² | Basis weight | 12.5 g/m² | Basis weight | 12.5 g/m² |
| Fibre | PP 3.3 dtex | Fibre | PET 7.0 dtex Solid | Fibre | PET 7.0 dtex Solid |
| Concentration | 85% | Concentration | 70% | Concentration | 70% |
| Fibre | bico PP/PE 3.3 dTex | Fibre | bico PP/PE 1.7 dTex | Fibre | bico PP/PE 1.7 dTex |
| Concentration | 15% | Concentration | 30% | Concentration | 30% |
| | | | Example B | | |
| Support Layer | | Bulky Layer N° 1 | | Bulky Layer N° 2 | |
| Basis weight | 15 g/m² | Basis weight | 15 g/m² | Basis weight | 15 g/m² |
| Fibre | PP 3.3 dtex | Fibre | PET 7.0 dtex Solid | Fibre | PET 7.0 dtex Solid |
| Concentration | 85% | Concentration | 70% | Concentration | 70% |
| Fibre | bico PP/PE 3.3 dTex | Fibre | Bico PP/PE 1.7 dTex | Fibre | Bico PP/PE 1.7 dTex |
| Concentration | 15% | Concentration | 30% | Concentration | 30% |

Example C

| Support Layer | | Bulky Layer N° 1 | | Bulky Layer N° 2 | |
|---|---|---|---|---|---|
| Basis weight | 15 g/m² | Basis weight | 15 g/m² | Basis weight | 15 g/m² |
| Fibre | PP 3.3 dtex | Fibre | PET 7.0 dtex Hollow | Fibre | PET 7.0 dtex Hollow |
| Concentration | 85% | Concentration | 70% | Concentration | 70% |
| Fibre | Bico PP/PE 3.3 dTex | Fibre | Bico PP/PE 1.7 dTex | Fibre | Bico PP/PE 1.7 dTex |
| Concentration | 15% | Concentration | 30% | Concentration | 30% |

Examples D & E

| Support Layer | | Bulky Layer N° 1 | | Bulky Layer N° 2 | |
|---|---|---|---|---|---|
| Basis weight | 15 g/m² | Basis weight | 10 g/m² | Basis weight | 20 g/m² |
| Fibre | PP 2.2 dtex | Fibre | PET 7.0 dtex Solid | Fibre | PET 7.0 dtex Solid |
| Concentration | 85% | Concentration | 70% | Concentration | 70% |
| Fibre | Bico PP/PE 3.3 dTex | Fibre | Bico PP/PE 1.7 dTex | Fibre | Bico PP/PE 1.7 dTex |
| Concentration | 15% | Concentration | 30% | Concentration | 30% |

D = when the bulky side is upwards; E = when the support layer is upwards/used as a coverstock

Example F

| Support Layer | | Bulky Layer N° 1 | | Bulky Layer N° 2 | |
|---|---|---|---|---|---|
| Basis weight | 10 g/m² | Basis weight | 10 g/m² | Basis weight | 10 g/m² |
| Fibre | PP 3.3 dtex | Fibre | Bico PP/PE 3.3 dTex | Fibre | PET 7.0 dtex Hollow |
| Concentration | 85% | Concentration | 100% | Concentration | 70% |
| Fibre | Bico PP/PE 3.3 dTex | Fibre | | Fibre | Bico PP/PE 1.7 dTex |
| Concentration | 15% | Concentration | | Concentration | 30% |

Example G

| Support Layer | | Bulky Layer N° 1 | | Bulky Layer N° 2 | |
|---|---|---|---|---|---|
| Basis weight | 10 g/m² | Basis weight | 8 g/m² | Basis weight | 8 g/m² |
| Fibre | PP 3.3 dtex | Fibre | Bico PP/PE 3.3 dTex | Fibre | PET 7.0 dtex Hollow |
| Concentration | 85% | Concentration | 100% | Concentration | 70% |
| Fibre | Bico PP/PE 3.3 dTex | Fibre | | Fibre | Bico PP/PE 1.7 dTex |
| Concentration | 15% | Concentration | | Concentration | 30% |

Example H

| Support Layer | | Bulky Layer N° 1 | | Bulky Layer N° 2 | |
|---|---|---|---|---|---|
| Basis weight | 15 g/m² | Basis weight | 15 g/m² | Basis weight | 15 g/m² |
| Fibre | PP 3.3 dtex perm. hydrophilic finish | Fibre | PET 7.0 dtex Hollow | Fibre | PET 7.0 dtex Hollow |
| Concentration | 85% | Concentration | 70% | Concentration | 70% |
| Fibre | Bico PP/PE 3.3 dTex | Fibre | Bico PP/PE 1.7 dTex | Fibre | Bico PP/PE 1.7 dTex |
| Concentration | 15% | Concentration | 30% | Concentration | 30% |

Example I

| Support Layer | | Bulky Layer N° 1 | | Bulky Layer N° 2 | |
|---|---|---|---|---|---|
| Basis weight | 10 g/m² | Basis weight | 10 g/m² | Basis weight | 10 g/m² |
| Fibre | PP 3.3 dtex | Fibre | PP 3.3 dtex | Fibre | PET 7.0 dtex Hollow |
| Concentration | 85% | Concentration | 100% | Concentration | 70% |
| Fibre | Bico PP/PE 3.3 dTex | Fibre | | Fibre | Bico PP/PE 1.7 dTex |
| Concentration | 15% | Concentration | | Concentration | 30% |

| | | 1st Strike through | Strike through | | | | | | | ADD | | | |
|---|---|---|---|---|---|---|---|---|---|---|---|---|---|
| Example | Basis weight g/m2 | Support up s | 3rd insult s | Rewet g | Retention % | 5 s g | 10 s g | 15 s g | Max g | T1 s | T2 s | T3 s | Wetback g |
| A | 40 | 1.32 | 0.94 | 0.13 | 1013.50 | 6.86 | 13.79 | 19.15 | 29.25 | 5.65 | 24.93 | 56.90 | 6.73 |
| B | 45 | 1.04 | 0.65 | 0.10 | 1141.31 | 7.93 | 14.22 | 20.76 | 34.42 | 5.63 | 19.60 | 43.04 | 7.37 |
| C | 45 | 1.41 | 0.75 | 0.12 | 1171.02 | 6.49 | 13.12 | 19.76 | 35.96 | 5.62 | 17.67 | 36.23 | 4.85 |
| D | 45 | — | 0.59 | 0.09 | 960.24 | 6.53 | 13.28 | 19.51 | 27.91 | 5.95 | 15.24 | 32.06 | 4.83 |
| E | 45 | 0.93 | — | 0.15 | 950.27 | 7.06 | 14.60 | 20.01 | 30.02 | 5.76 | 16.68 | 33.24 | 4.53 |
| F | 30 | 1.43 | 0.94 | 0.10 | 823.74 | 6.54 | 13.01 | 19.00 | 29.60 | 5.67 | 23.69 | 57.62 | 7.62 |
| G | 26 | 1.47 | 1.48 | 0.10 | 823.74 | 7.00 | 13.70 | 17.90 | 26.19 | 5.40 | 24.29 | 50.88 | 7.18 |
| H | 45 | 0.68 | 0.70 | 0.09 | 968.88 | 5.21 | 9.93 | 14.35 | 35.03 | 5.87 | 15.56 | 26.40 | 3.75 |
| I | 30 | 1.17 | 0.85 | 0.10 | 984.26 | 6.23 | 13.72 | 19.89 | 29.85 | 5.71 | 26.00 | 54.32 | 6.36 |

We claim:

1. A composite nonwoven for acquisition and distribution of liquid, comprising:

at least a first support layer and a first bulky layer, the bulky layer functioning to acquire and distribute liquid and the support layer being suitable for use either as a coverstock or as a transfer layer between the bulky layer and a liquid retention layer, the support layer and the bulky layer being bonded together by a network of individual bonding points to form a liquid control system that facilitates liquid distribution within the individual layers and liquid transfer between the layers, the composite nonwoven showing a combination of a strike-through time at the third insult of at the most about 2.5 sec or an acquisition time at the third insult of at most about 60 sec, and a rewet value of at most about 0.20 g or a wetback value of at most about 7 g.

2. A composite nonwoven according to claim 1 wherein the support layer and the bulky layer are bonded together by non-chemical bonding means.

3. A composite nonwoven according to claim 1 which contains a second bulky layer, the second bulky layer being bonded to the first bulky layer by a network of individual bonding points to form a liquid control system that facilitates liquid distribution within the individual layers and liquid transfer between the bulky layers.

4. A composite nonwoven according to claim 1 comprising at least one bulky layer comprising a mix of synthetic binder fibres and matrix fibres, said binder fibres being selected from bicomponent fibres and monocomponent fibres containing polyethylene, polypropylene, polyester or a copolymer, and said matrix fibres being selected from polypropylene, polyester and cellulosic fibres, including viscose fibres.

5. A composite nonwoven according to claim 4 wherein the binder fibres are polypropylene/polyethylene, polyester/polyethylene or polyester/copolyester bicomponent fibres and the matrix fibres are polyester fibres.

6. A composite nonwoven according to claim 1 wherein the support layer is a carded or spunbonded web.

7. A composite nonwoven according to claim 1 wherein the support layer comprises polypropylene and/or bicomponent fibres or filaments.

8. A composite nonwoven according to claim 1 wherein the support layer comprises fibres or filaments having a fineness in the range of 1–7 dtex.

9. A composite nonwoven according to claim 1 comprising at least one bulky layer comprising bicomponent fibres with a fineness in the range of 1–7 dtex and matrix fibres with a fineness in the range of 1–12 dtex.

10. A composite nonwoven according to claim 9 which comprises at least one bulky layer designed primarily for acquisition of liquid and comprising matrix fibres having a fineness in the range of 5–12 dtex, and at least one bulky layer designed primarily for distribution of liquid within the layer and comprising matrix fibres having a fineness in the range of from 1 to less than 5 dtex.

11. A composite nonwoven according to claim 1 comprising bicomponent fibres and/or polypropylene fibres or filaments treated with a permanent hydrophilic spin finish.

12. A composite nonwoven according to claim 1 comprising at least one bulky layer comprising fibres with a 3-dimensional crimp and/or hollow fibres.

13. A composite nonwoven according to claim 1 wherein the first support layer has a basis weight of at the most 20 g/m$^2$, the total basis weight of the bulky layer(s) being in the range of 8 to 60 g/m$^2$.

14. A composite nonwoven according to claim 4 wherein the percentage of binder fibres in the bulky layer(s) is in the range of 10–65% by weight, based on the total weight of the bulky layer(s).

15. A high-speed in-line process for producing a composite nonwoven for acquisition and distribution of liquid comprising at least a first support layer and a first bulky layer, the bulky layer functioning to acquire and distribute liquid and the support layer being suitable for use either as a coverstock or as a transfer layer between the bulky layers and a liquid retention layer, the process comprising forming a first support layer, consolidating the first support layer, forming a first bulky layer containing carded fibres on top of the first support layer, and bonding the combination of the support layer and the bulky layer by non-chemical bonding to form bonds within the bulky layer and a network of individual bonding points between the first bulky layer and the first support layer that facilitate liquid distribution within the individual layers and liquid transfer between the layers, during which process draft is reduced at least during formation of the first bulky layer by means of at least one laydown suction box providing suction at least at the point at which the bulky layer is formed and by means of at least one holddown suction box providing suction after formation of the bulky layer and until the point at which bonding between the layers takes place, said laydown and holddown suction boxes being located beneath an air-permeable conveyor belt; wherein the composite nonwoven has a combination of a strike-through time at the third insult of at the most about 2.5 sec or an acquisition time at the third insult of at most about 60 sec, and a rewet value of at most about 0.20 g or a wetback value of at most about 7 g.

16. A process according to claim 15 which further includes the step of forming a second bulky layer on top of the first bulky layer before bonding of the first support layer and the first bulky layer, the second bulky layer being subsequently bonded to the first bulky layer by a network of individual bonding points that facilitate liquid transfer between the bulky layers.

17. A process according to claim 16 in which the second bulky layer is a carded layer formed using a second card in opposite orientation to the card forming the first bulky layer, and using a perforated suction roll at the point at which the second bulky layer is laid onto the first bulky layer, wherein draft is reduced during formation of the second bulky layer by means of at least one suction box providing suction between the card exit for the second bulky layer and the perforated suction roll.

18. A process according to claim 15 in which consolidation of the first support layer is performed by means of thermobonding, infrared bonding or ultrasonic bonding.

19. A process according to claim 18 wherein the first support layer is produced by carding and wherein, during formation of the first support layer, draft is reduced from the card exit point and until the point at which consolidation takes place by means of at least one suction box.

20. A process according to claim 19 wherein consolidation of the first support layer is performed using calender bonding means including at least upper and lower calender rolls, the first support layer being transported to the calender bonding means on a conveyor belt, in which the calender bonding means has an arrangement between the conveyor belt and the calender rolls that allows the upper calender roll to function as a rotating support for the unbonded first support layer, and in which the conveyor belt has a reduced diameter conveyor head roll that allows a reduced distance between the conveyor head roll and the upper and lower calender rolls, the distance between the conveyor head roll and the upper calender roll being essentially the same as or not substantially greater than the thickness of the first support layer to be consolidated using the calender bonding means.

21. A process according to claim 15 wherein the first support layer is produced by spunbonding.

22. A process according to claim 15 in which the bonding of the first bulky layer to the first support layer and, when present, to the second bulky layer, is performed using a through-air oven which can be adjusted to allow either the support layer or the first bulky layer or, when present, the second bulky layer to be in contact with the drum of the oven.

23. A process according to claim 15 in which air sucked from each suction box is recycled, filtered and adjusted to a desired temperature and relative humidity by an air conditioning system.

24. A process according to claim 15 in which static electricity repellency between the conveyor belts and the fibres of any of the layers is reduced by means of humidified air having a relative humidity of 45–65% being sucked through the fibrous webs and the conveyor belts.

25. A process according to claim 18 wherein consolidation of the first support layer is performed using calender bonding or a hot-air oven.

26. A composite nonwoven according to claim 1 which exhibits at least one of the following properties:
a) a strike-through time ($3^{rd}$ insult) of at the most about 2.0 sec;
b) a rewet of at the most about 0.15 g;
c) an acquisition time ($3^{rd}$ insult) of at the most about 40 sec; and
d) a wetback of at the most about 5 g.

27. A composite nonwoven according to claim 26 which exhibits at least one of the following properties:
a) a strike-through time ($3^{rd}$ insult) of at the most about 1.5 sec;
b) a rewet of at the most about 0.10 g;
c) an acquisition time ($3^{rd}$ insult) of at the most about 30 sec; and
d) a wetback of at the most about 4 g.

28. A composite nonwoven according to claim 8 wherein the support layer comprises fibres or filaments with a fineness in the range of 1.5–5 dtex.

29. A composite nonwoven according to claim 9 wherein at least one bulky layer comprises bicomponent fibres with a fineness in the range of 1.5–5 dtex.

30. A composite nonwoven according to claim 13 wherein the first support layer has a basis weight of at the most 16 g/m$^2$, and the total weight of the bulky layer(s) is in the range of 12–40 g/m$^2$.

* * * * *